(12) United States Patent
Sutter

(10) Patent No.: US 6,461,160 B1
(45) Date of Patent: Oct. 8, 2002

(54) DEVICE FOR HOLDING AND/OR CREATING A DENTAL PROSTHESIS

(76) Inventor: Franz Sutter, Bennwilerstrasse 42, CH-4435 Niederdorf (CH)

( * ) Notice: Subject to any disclaimer, the term of this patent is extended or adjusted under 35 U.S.C. 154(b) by 0 days.

(21) Appl. No.: 09/744,651
(22) PCT Filed: Jul. 28, 1999
(86) PCT No.: PCT/CH99/00352
§ 371 (c)(1),
(2), (4) Date: Jan. 29, 2001
(87) PCT Pub. No.: WO00/06042
PCT Pub. Date: Feb. 10, 2000

(30) Foreign Application Priority Data

Jul. 29, 1998 (CH) .............................................. 1593/98

(51) Int. Cl.[7] ................................................ A61C 8/00
(52) U.S. Cl. ...................................... 433/173; 433/172
(58) Field of Search ................................. 433/172, 173, 433/174, 175, 176, 201.1

(56) References Cited

U.S. PATENT DOCUMENTS

| | | | | |
|---|---|---|---|---|
| 4,468,200 A | * | 8/1984 | Munch | 433/174 |
| 4,486,178 A | * | 12/1984 | Schulte | 433/173 |
| 4,531,915 A | * | 7/1985 | Tatum, Jr. | 433/173 |
| 5,302,126 A | * | 4/1994 | Wimmer et al. | 433/173 |
| 5,368,483 A | * | 11/1994 | Sutter et al. | 433/173 |
| 5,888,066 A | * | 3/1999 | Morgan | 433/172 |
| 5,961,328 A | * | 10/1999 | Samborac et al. | 433/173 |
| 6,024,567 A | * | 2/2000 | Callan | 433/173 |

* cited by examiner

Primary Examiner—John J. Wilson
(74) Attorney, Agent, or Firm—Venable; Catherine M. Voorhees

(57) ABSTRACT

The device (75) for holding and/or creating a dental prosthesis comprises an implant (1) with an axis (3) and with a metal main body (50) which forms at least a large part of an anchoring part (5) intended to be anchored in a bone (71) and has an axial hole (35). A ceramic body (60) or covering is also connected nonreleasably and directly to the main body (50). A metal metal [sic] bolt (80) which can be secured in the hole (35) of the main body (50) protrudes into a blind hole (91) of a ceramic body (90) which is rigidly and nonreleasably secured on the bolt (80) and covers the end of same directed away from the main body (50), and if necessary can be ground after insertion into the mouth of a patient and permits rapid and simple impression-taking.

38 Claims, 11 Drawing Sheets

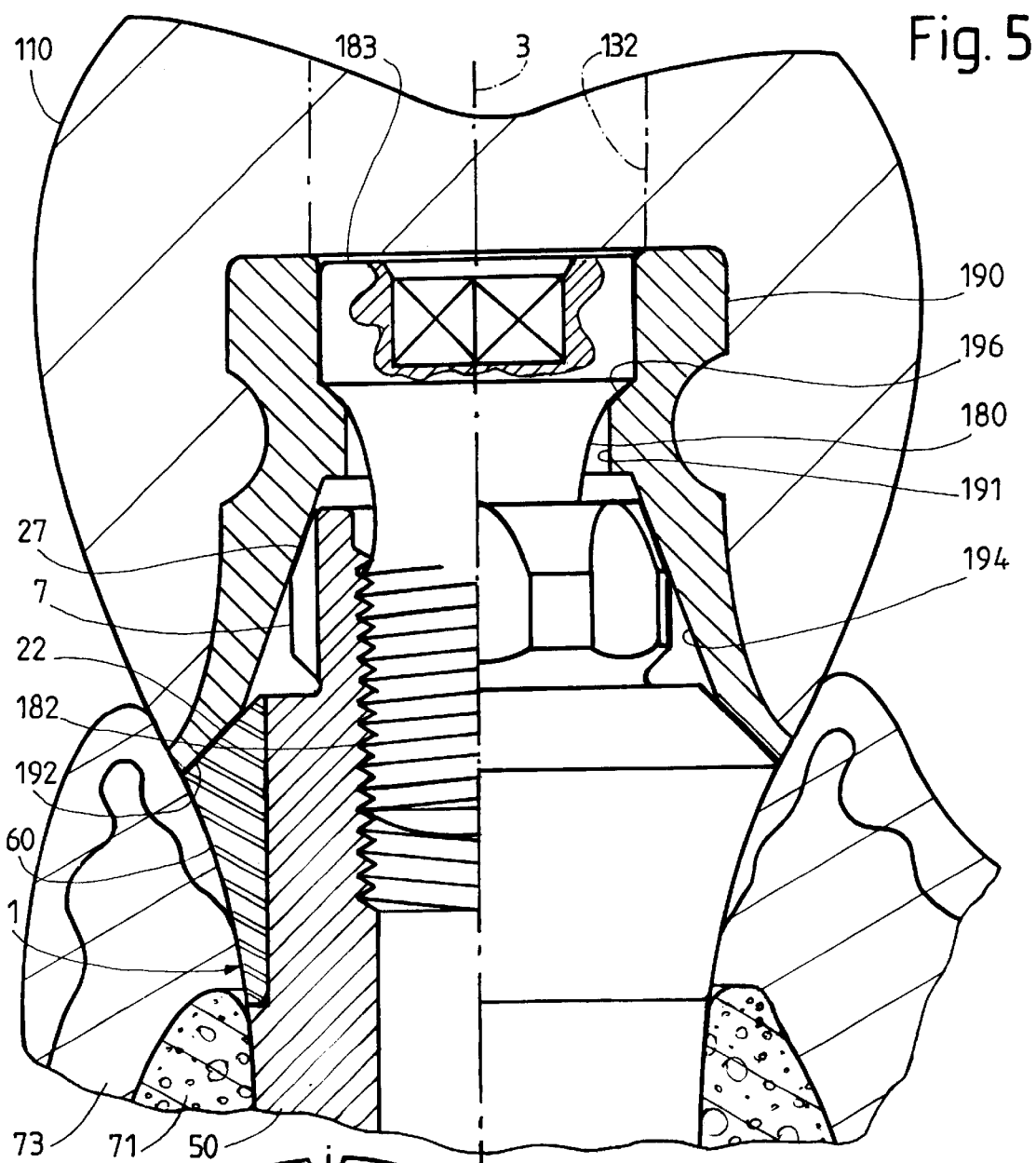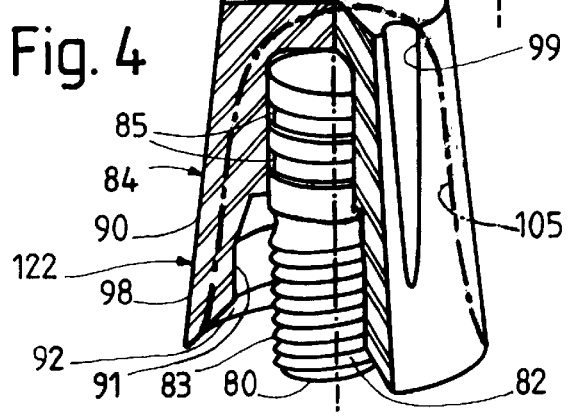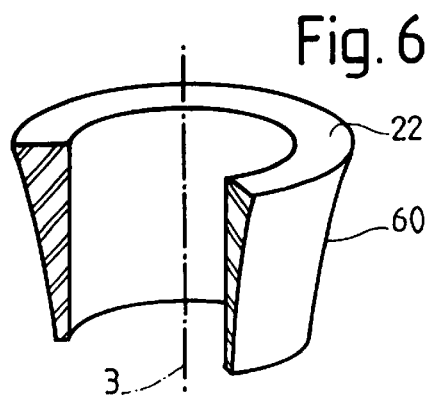

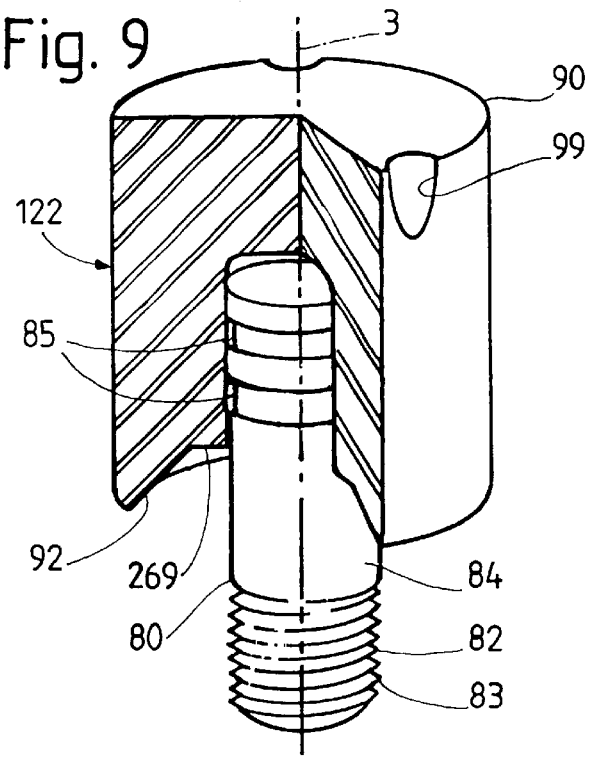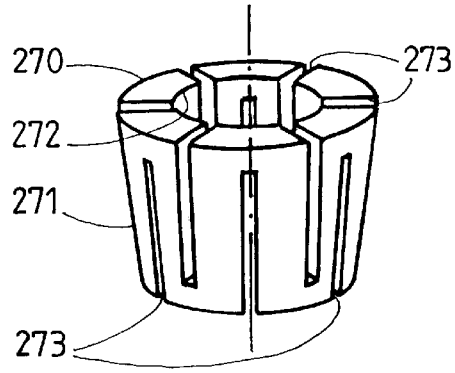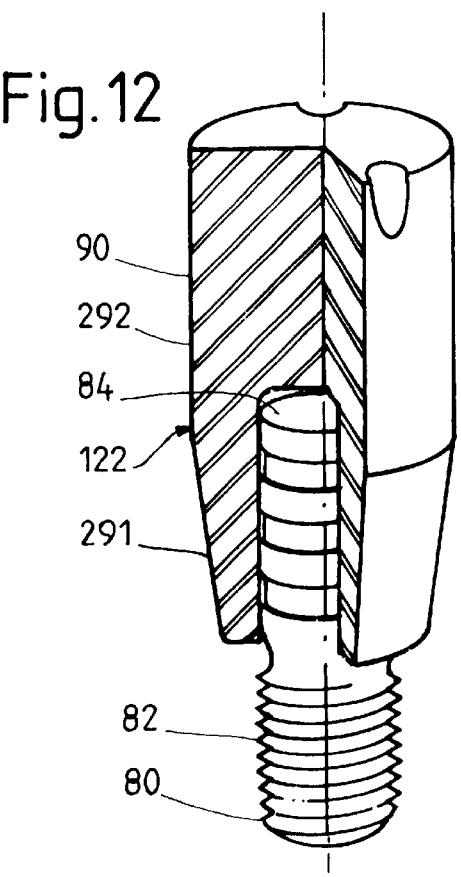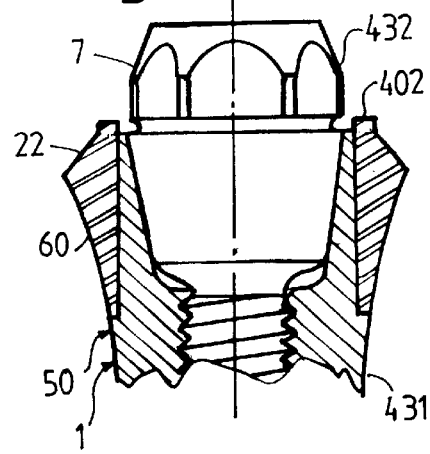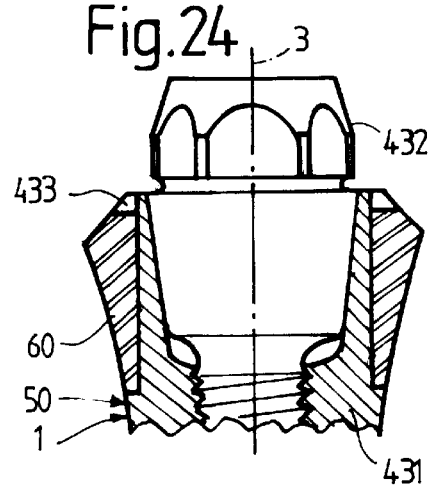

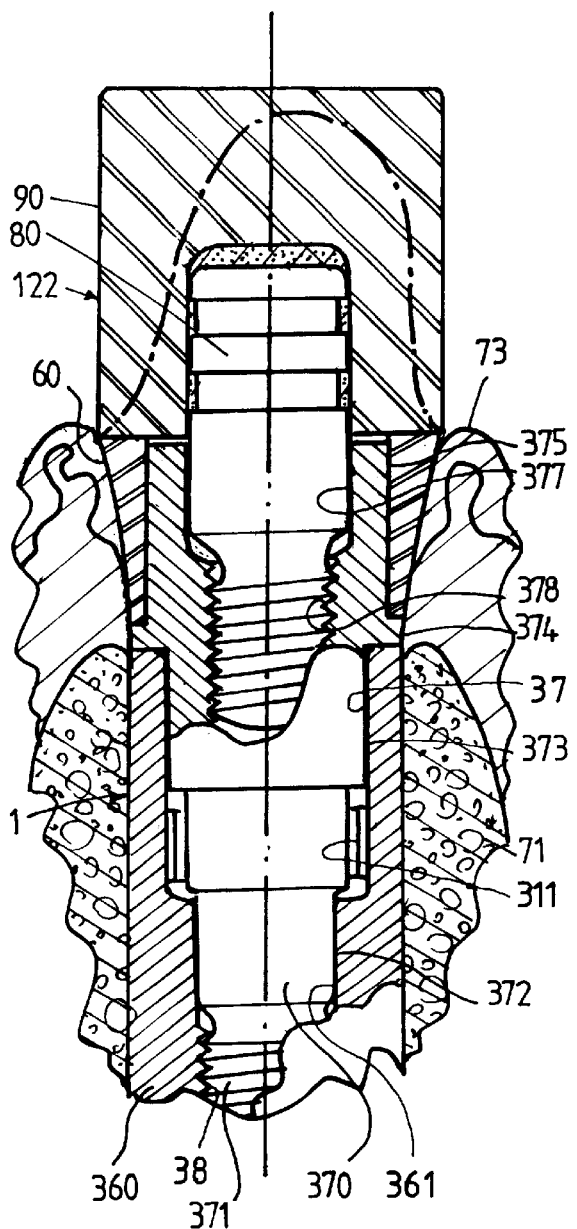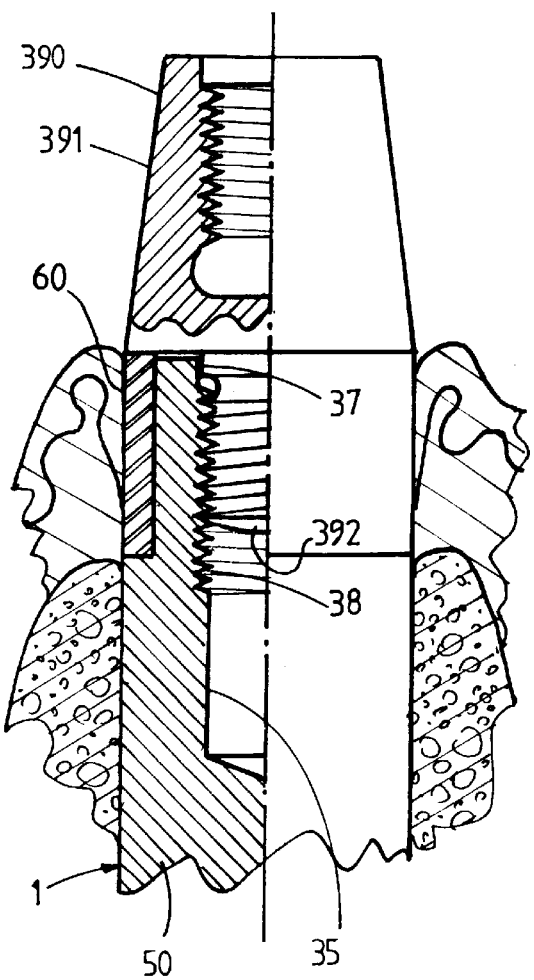

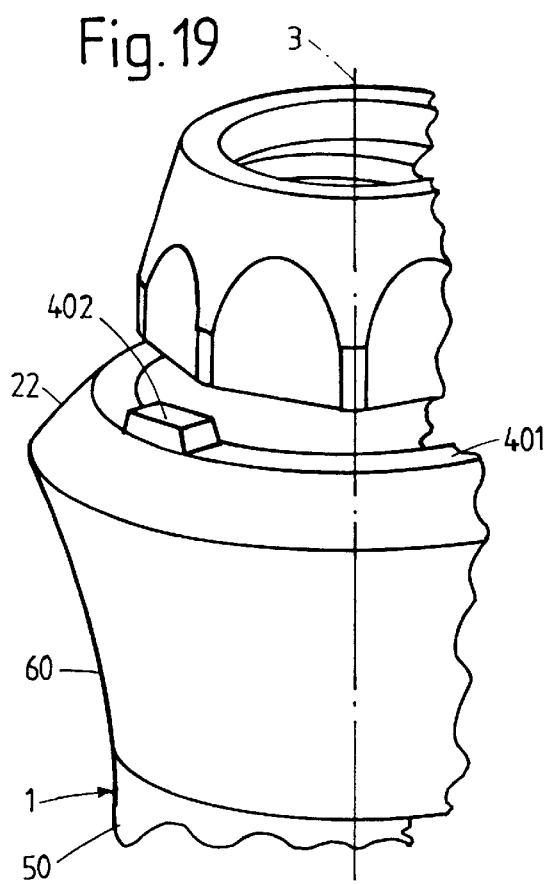
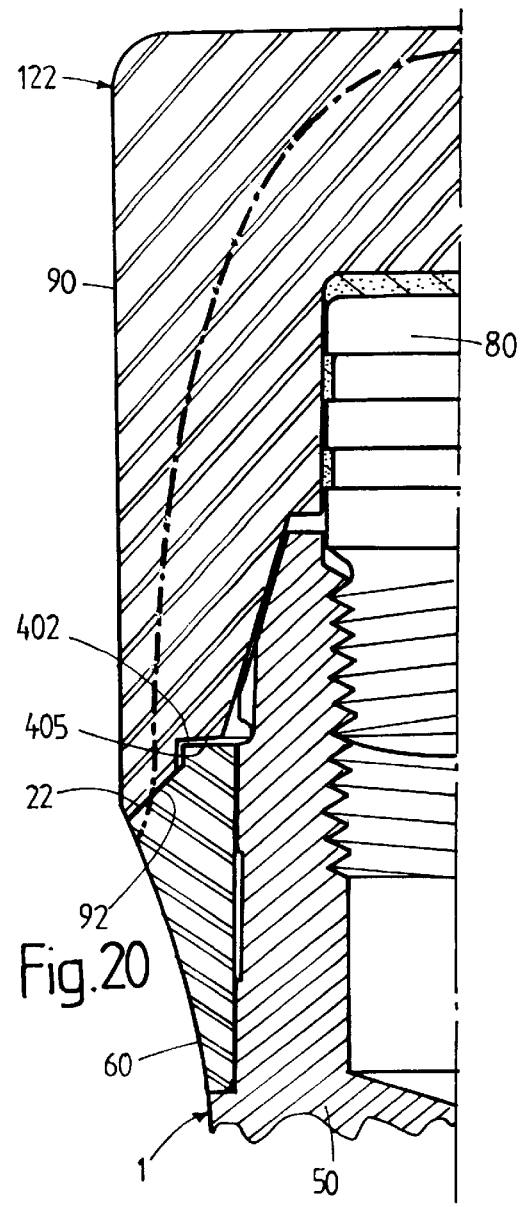
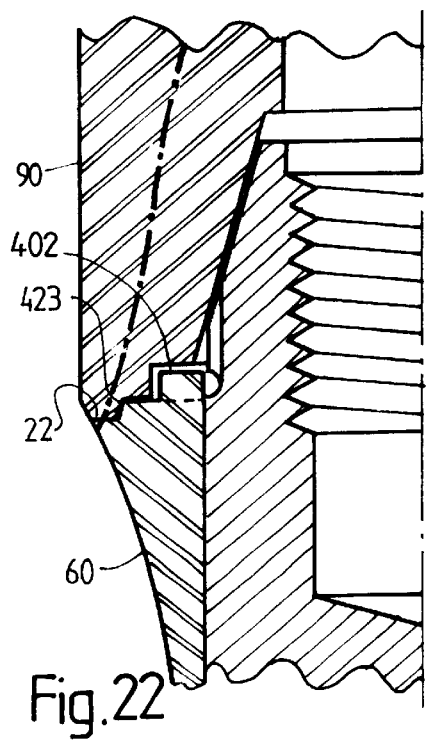
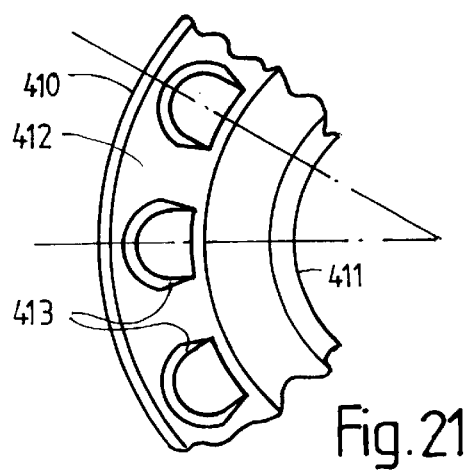

DEVICE FOR HOLDING AND/OR CREATING A DENTAL PROSTHESIS

BACKGROUND OF THE INVENTION

The invention relates to a device for holding and/or creating a dental prosthesis, with a metal main body intended to be at least partially anchored in a bone and having a hole, and with a metal bolt which can be secured in the hole of the main body and which protrudes into a hole of a ceramic body and is rigidly connected thereto. The dental prosthesis can be, for example, a single artificial tooth, a bridge, or a prosthesis comprising a plurality of teeth.

Many known devices for creating a dental prosthesis comprise an implant which can be implanted into a bone and is made of titanium or a titanium alloy, and an abutment element which lies on the implant in the area of the soft tissue and/or slightly above the latter. However, an implant with a metal surface contiguous with the soft tissue sometimes causes irritations and inflammation of the soft tissue. The abutment element is sometimes made of gold or a gold alloy. If parts with outer surfaces made from different metal materials come into contact with each other in the area of the soft tissue or in the oral cavity, these parts, together with the acid-containing saliva and/or the tissue fluid, can act as a galvanic element, generate an electric current and cause additional irritations. Known devices often have a conical or cylindrical pier made of titanium or titanium alloy which projects from the implant and on which a crown or another abutment element is mounted. Such metal piers have the disadvantage that they are poorly adaptable to individual shapes in the mouth of a patient. One reason for this is that, for example when grinding such a part, unwanted metal particles arise and get into the patient's mouth. If a porcelain crown is applied to a metal pier, the pier often also causes an esthetically unwelcome matt hue of the porcelain crown.

To avoid irritations of the soft tissue, it is known to provide devices with a ceramic body in the area of the soft tissue. For example, U.S. Pat. No. 5,310,343 discloses devices with a metal main body and with a metal bolt, which can be screwed together with the latter. The main body and the bolt have, in cross section, portions surrounded by ceramic material. However, at its end protruding from the main body, the bolt has an open hexagonal hole, i.e. one not covered by ceramic material If, after the device has been inserted into the mouth of a patient, an impression of the device and of the teeth adjacent to it is made, the hexagonal hole should however be temporarily sealed for impression-taking. This makes impression-taking more time-consuming and more complicated. Moreover, it would often be desirable for the ceramic material secured on the bolt to be ground also in the central area in order to permit optimum adaptation of the shape to the individual situation. However, because of the hexagonal hole, this too is not possible. In these known devices, a metal flange of the bolt is present between the ceramic material arranged on the main body and the ceramic material arranged on the bolt. This metal flange can come into contact with the soft tissue and may be visible from outside and thus impair the effects, which are sought using the ceramic material. Moreover, the ceramic material cannot be ground continuously from the level of the bolt to the level of the main body without also grinding the metal flange. No metal parts should be ground inside the mouth of a patient, however, since metal chips then get into the patient's mouth. In the devices known from U.S. Pat. No. 5,310,343, the hole of the main body and the bolt have conical portions fitting into each other. Moreover, the main body and the ceramic material arranged on it together form a plane annular surface toward which a plane annular face of the flange is directed when the device is assembled. Because of the manufacturing inaccuracies, however, either only the conical portions of the main body hole and bolt or only said plane annular surfaces can lie on each other free of gaps. If the conical portions do not lie on each other free of gaps, the upper bolt portion, the ceramic material arranged thereon, and an abutment mounted on the latter can execute micro movements directed transversely with respect to the axis of the main body. If, by contrast, a gap is present between the annular surfaces, microorganisms can penetrate into this gap. Both said micro movements and penetrating microorganisms can jeopardize the permanent securing of the device in the mouth of a patient.

SUMMARY OF THE INVENTION

The object of them invention is to avoid disadvantages of the known devices and in particular to make available a device which, after insertion into a mouth of a patient, permits rapid and simple impression-taking and casting, and whose parts protruding from the bone can, if so desired, be ground within the patient's mouth without any problem. In addition, the device is preferably intended to ensure that no microorganisms can penetrate between the main bodies and the bolt and the ceramic body secured on the latter, and that the ceramic body secured on the bolt is connected to the metal main body in a very stable manner so that, even under the effect of substantial forces acting approximately transversely with respect to the axis of the main body, this ceramic body as far as possible executes no movements relative to the main body. In addition, for creating a dental prosthesis in the mouth of a patient, the device is intended to be able to be assembled from as few separate parts as possible.

This object is achieved by means of a device for holding and/or creating a dental prosthesis including a metal main body adapted to be at least partially anchored in a bone with a hole, a metal bolt which is secured in the hole of the main body, and a ceramic body with a hole to which the metal bolt is rigidly connected wherein the hole of the ceramic body is a blind hole in that it has an end directed away from the main body and the end is closed off by ceramic material of the ceramic body.

Advantageous embodiments of the device will be evident from the dependent claims.

The device design according to the invention permits, after insertion of the device into a patient's mouth, rapid and simple impression-taking, i.e. casting of those device parts protruding from the bone and passing through the soft tissue. In particular, it is not necessary, for impression-taking, to temporarily cover any hole of the ceramic body secured on the bolt and/or of the bolt itself. In addition, if necessary, the central portion of the ceramic body secured on the bolt, covering the bolt end protruding from the main body, can be ground in the patient's mouth area.

The device moreover permits a rigid, stable, permanent and indirect connection of the metal main body to the ceramic body secured on the bolt. In addition, in order to create a dental prosthesis in the mouth of a patient, a dentist has to assemble only a small number of separate parts.

In an advantageous embodiment of the device, the main body has an axial portion surrounded in cross section by ceramic material. This ceramic material and the ceramic body secured on the bolt consist, for example, of originally separate ceramic bodies. The ceramic body secured on the main body, and the ceramic body secured on the bolt, are connected directly to the main body or bolt, respectively, by means of a binder. Depending on the design of the parts to be connected to each other, the binder can consist of a thinly fluid adhesive to be applied in a thin layer, or of a relatively viscous adhesive or cement, which is suitable for filling at least one relatively large interspace. When joining the parts together, the adhesive and/or cement can set at normal room temperature, for example, or can be heated to allow setting. Instead of being joined by an adhesive or cement, the or each ceramic body may possibly be connected to the metal main body or bolt by means of a hard solder connection. In this case, the binder then consists of a hard solder which is temporarily heated and melted when connecting the ceramic body to the metal main body or bolt. The binder must in all cases be biocompatible, nontoxic, and well tolerated by the bones and soft tissues of patients. The ceramic body can furthermore form a press-fit together with the main body or the bolt and, instead of using a binder, or in addition to such a binder, can be connected to the main body or bolt by a press-fit connection.

The or each ceramic body can be shaped separately—i.e. separate from the main body and relevant bolt—for example using a plastically deformable mass which comprises particles and is more or less easily flowing, and with the aid of a casting mold or the like, in such a way that it is at least substantially rotationally symmetrical with respect to an axis. Before being connected to a main body or bolt, the shaped body is then heated and sintered in the usual way. If two ceramic bodies are present, one or either of them, when used to create a dental prosthesis, can if necessary be ground further in places in the mouth of a patient by a dentist and thereby individually shaped on production of an abutment element or superstructre.

The ceramic material, or at least part thereof, secured preferably directly on the main body can furthermore form a ceramic covering connected to the main body in a nonreleasable manner. The ceramic covering can be applied, for example sprayed, nonreleasably onto an area of the metal main body. This covering can consist of a thin layer whose thickness is for example at most 100 μm only, and for example approximately 50 μm.

The metal main body, and the metal bolt secured in the hole of the main body, can be made of titanium or a titanium alloy, for example. The or each ceramic body and/or the ceramic covering preferably consists of oxide ceramic, for example aluminum oxide and/or magnesium oxide and/or zirconium oxide, and is preferably electrically insulating.

BRIEF DESCRIPTION OF THE DRAWINGS

The subject of the invention and further advantages thereof will now be explained in greater detail with reference to illustrative embodiments represented in the drawings, in which FIG. 4 shows an oblique view of parts of the device according to FIG. 3, FIG. 5 shows a section through the implant according to FIG. 1, and another abutment element secured thereon, FIG. 6 shows an oblique view of a variant of a cut-open ceramic body, FIGS. 9 and 10 show oblique views of parts of the device according to FIG. 8, FIG. 12 shows an oblique view of parts of the device shown in FIG. 11, FIG. 19 shows an oblique view of an implant with a ceramic body having at least one protuberance, FIG. 20 shows an axial section through parts of a device with an implant according to FIG. 19, FIG. 21 shows a view of a portion of a nonrotationally positionable body fitting the implant according to FIG. 19, FIG. 22 shows an axial section through a device with another implant whose ceramic body has at least one protuberance, FIG. 23 shows an axial section through another implant with protuberances, and FIG. 24 shows an axial section through an implant with a ceramic body comprising recesses.

DETAILED DESCRIPTION OF THE INVENTION

As regards the illustrative embodiments described below, it should be noted that corresponding identical or similar parts of the various illustrative embodiments are in each case labeled with the same reference number.

Figure 1:
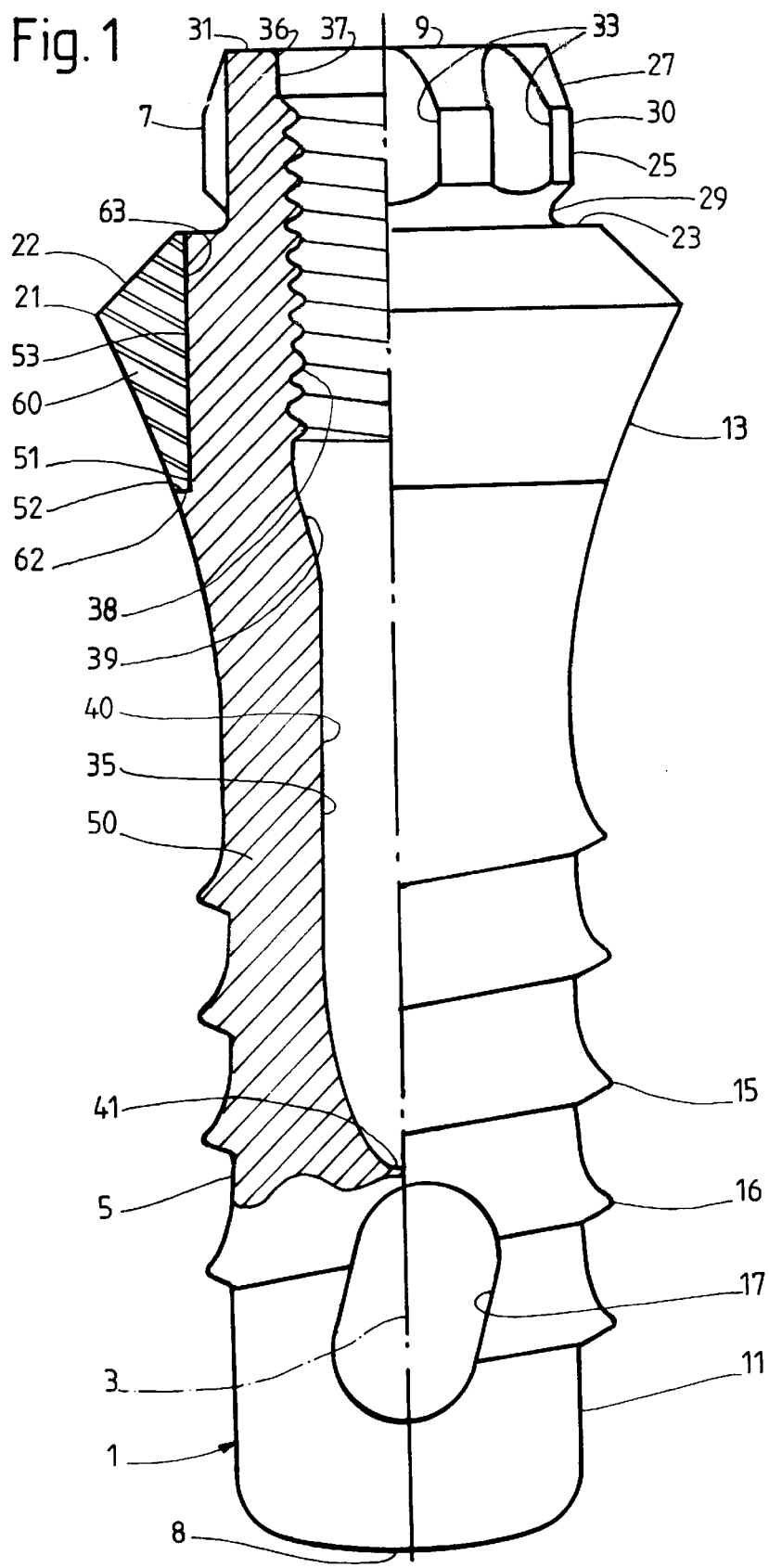
FIG. 1 shows an implant, partly in side view and partly in section, with a metal main body and with a ceramic body secured on the latter.

The implant 1 shown in FIG. 1 is generally rotationally symmetrical with respect to an axis 3 and at the bottom has an anchoring part 5 intended to be anchored in a bone of an upper or lower jaw, and at the top has a head 7 intended to protrude from the bone. The free ends of the anchoring part and of the head directed away from each other form the first end 8 and the second end 9, respectively, of the implant 1. Viewed from the bottom upward, the anchoring part 5 has a generally cylindrical portion 11 and, widening away from this, a trumpet-shaped portion 13 whose outer surface merges continuously and smoothly with the outer surface of the generally cylindrical portion 11. The generally cylindrical portion 11 is provided with an external thread 15 with a helical rib 16. The external thread 15 is, for example, self-tapping. Near its lower end, the anchoring part is provided with several, for example three, elongate grooves and/or holes 17 which are distributed around the axis 3 and which intersect the helical rib 16 of the external thread.

At the upper, wider end of the trumpet-shaped portion 13 there is a shoulder 21 with a conical shoulder surface 22 inclined upward and inward in the direction away from the first end 8. This shoulder surface 22 forms, with the axis 3, an angle of 40° to 50°, for example 45°. Contiguous with the upper, narrower end of the conical shoulder surface 22 there is a plane annular surface 23 at right angles to the axis 3.

The head 7 protrudes upward from the annular surface 23, is generally rotationally symmetrical with respect to the axis 3 and has a generally cylindrical head portion 25 substantially parallel with the axis 3, and a generally conical head portion 27 tapering upward from the head portion 25 to the free end of the head and thus to the second end 9 of the whole implant. The two head portions 25, 27 each have an enveloping surface rotationally symmetrical with respect to the axis, namely cylindrical and conical, respectively. The maximum diameter of the head is smaller than the diameters of the outer edge and also of the inner edge of the conical shoulder surface 22. The conical enveloping surface of the generally conical head portion 27 forms, with the axis 3, an angle which is smaller than the angle formed by the conical shoulder surface 22 with the axis and is preferably 15° to 25°, for example approximately 20°. The head portion 25 parallel with the axis is delimited from the upper end of the shoulder 21 by an annular groove 29 which is concave in cross section. The head has a peripheral surface 30 and, at its free end, a plane annular end face 31 forming the second end 9 of the implant. The peripheral surface 30 of the head 7 has protuberances and interspaces successively alternating around the axis. The interspaces consist of axial grooves 33 which are arcuate in cross section, for example, but instead of this can be V-shaped, trapezoid or rectangular. Several identically configured and dimensioned first grooves and a wider and/or deeper second groove are preferably present. The deepest areas of the grooves 33 in cross section extend along the entire length of the head portion 25 parallel with the axis 3 and at least approximately, and for example exactly, as far as the thinner end of the conical head portion 27 and thus also as far as the second end 9 of the whole implant.

The implant 1 is provided with a blind hole 35 coaxial to the axis 3. This blind hole 35 has a mouth 36 situated at the second end 9 and surrounded by the annular end face 31, and, moving down from this in succession, a short, smooth first cylindrical hole portion 37, a for example metric internal thread 38, a transition portion 39, a second cylindrical smooth, i.e. threadless, hole portion 40, and a base 41. The lower end of the internal thread 38 farther from the mouth is situated within the widening, trumpet-shaped portion 13 of the implant. The diameter of the second cylindrical hole portion 40 is smaller than that of the first cylindrical hole portion 37 and approximately equal to the core diameter of the internal thread. The transition portion 39 consists of a fairly flat annular groove and has a surface which is continuously curved in axial section and merges continuously with the cylindrical surface of the second cylindrical hole portion. The base 41 tapers to its deepest point and is delimited by a surface which is curved in axial section and which merges continuously and smoothly with the surface of the second cylindrical hole portion 40.

Figures 2, 3:
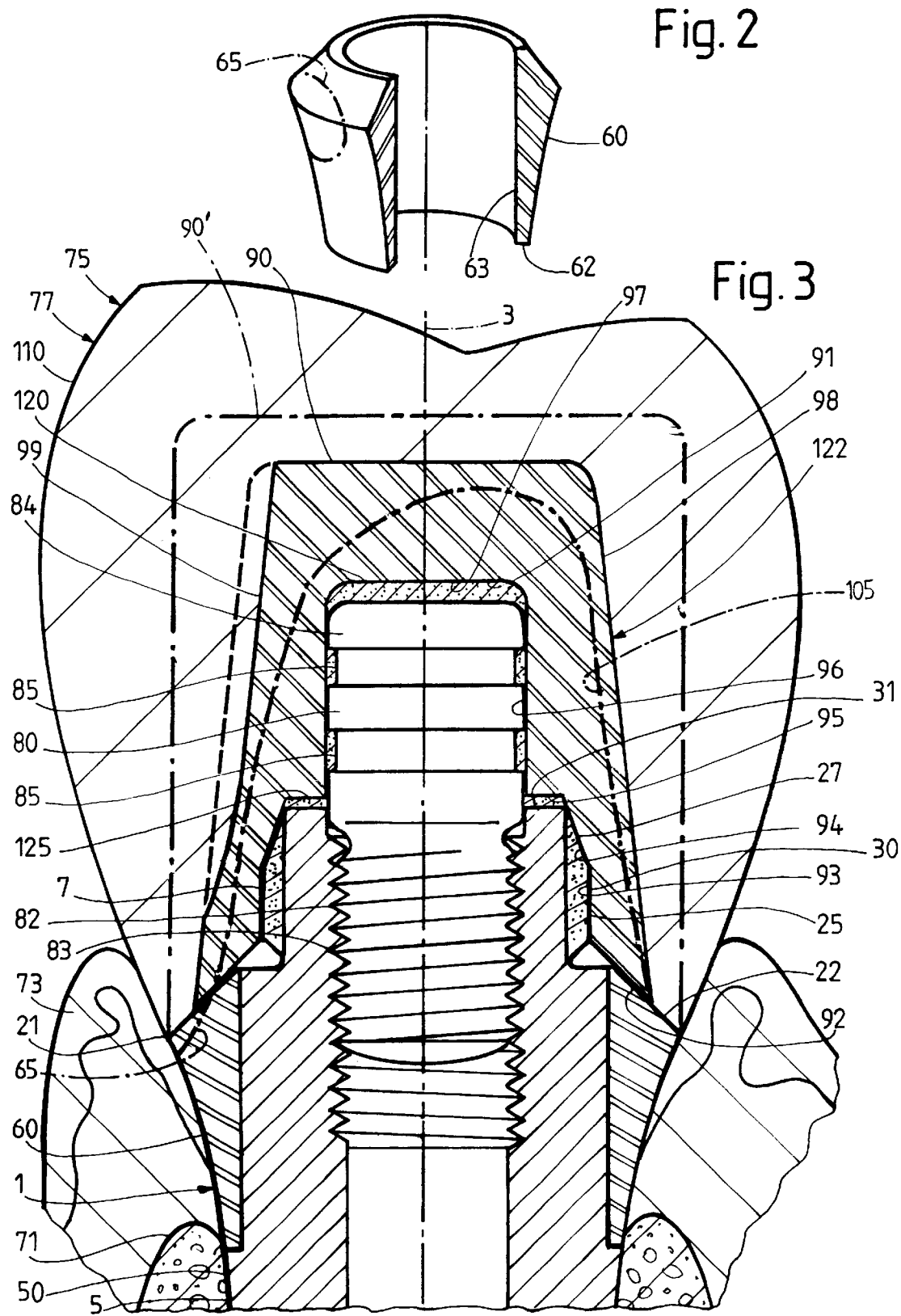
FIG. 2 shows the ceramic body separately, cut open and represented in an oblique view.
FIG. 3 shows a section through a device with the implant according to FIG. 1 inserted in a bone, and an abutment element secured thereon.

The implant 1 consists of two originally separate one-piece bodies, namely an elongate metal main body 50 and an annular and/or sleeve-shaped ceramic body 60, still shown as separate in FIG. 2. The metal main body 50 forms the greater part of the implant 1 and extends from the first end 8 to the second end 9 of the implant. The metal main body 50 also in particular forms at least the greater part of the anchoring part 5, the whole external thread 15 and the whole head 7 and the whole limit of the blind hole 35. The ceramic body 60 forms that area of the outer and/or peripheral surface of the implant situated in the environs of the shoulder 21, namely the upper area of the peripheral surface of the trumpet-shaped portion 13, the conical shoulder surface 22 and the outer edge area of the plane annular surface 23. At the level of the shoulder 21, the metal main body 50 has an annular throat 51 surrounding the axis 3 and the blind hole 35. This throat 51 is formed and/or delimited by a stop surface 52, arranged at the lower end of the throat, and by a neck surface 53. The stop surface 52 is situated approximately at the level of the transition portion 39 of the blind hole 35. The neck surface 53 protrudes upward from the stop surface 52, defines a neck of the main body and extends as far as the plane annular surface 23.

The ceramic body 60 has, at the lower end, an annular bearing surface 62, and an inner surface 63 extending from this as far as the upper end of the ceramic body. The stop surface 52 of the main body 50 and the bearing surface 62 of the ceramic body 60 form, with the axis 3, an at least approximately right angle and indeed an exactly right angle. The two surfaces 52, 62 are accordingly plane. The neck surface 53 of the main body 50 and the inner surface 63 of the body 60 are at least approximately parallel with the axis and indeed exactly parallel with this and cylindrical. The inner surface 63 of the ceramic body 60 surrounds the neck surface 53 of the metal main body 50 for example with slight radial play. The radial distance of the inner surface 63 from the neck surface 53 is preferably at most 200 $\mu$m and for example 5 $\mu$m to 50 $\mu$m. The ceramic body 60 is connected nonreleasably to the main body 50 by means of a binder. The binder consists of a thinly fluid adhesive applied in a thin layer, is arranged between the two cylindrical surfaces 53, 63 and connects them to each other. The two plane surfaces 52 and 62 lie on each other without a gap, for example without binder arranged between them, but they can likewise be connected to each other by means of a binder, if appropriate. After the binder has set, the metal main body 50 and the ceramic body 60 together form a rigid indivisible unit. The peripheral surface areas of the trumpet-shaped portion 13, which are formed by the metal main body 50 and by the ceramic body 60, can be designed, when producing the two bodies 50, 60, in such a way that, after the two bodies have been glued, they can be joined to each other in a practically smooth, stepless and seamless manner without any reworking of said bodies.

FIG. 3 shows a bone 71, for example the lower jaw, the soft tissue 73 covering the latter—i.e. the gingiva—of a patient, and a device 75. The device 75 has an implant 1 designed in accordance with FIG. 1 and fitted in the bone 71, a metal bolt 80 and an abutment element 77 or superstructure with a one-piece ceramic body 90 and a crown 110. The bolt 80 and the body 90 are also shown in FIG. 4.

The metal bolt 80 has a threaded portion 82 with an external thread 83, and a cylindrical threadless portion 84 whose external diameter is equal to the external diameter of the threaded portion 82 or slightly greater than the last-mentioned diameter. The cylindrical portion 84 is provided with at least one annular groove 85 and for example with two or even more such grooves. An annular groove which is concavely curved in axial section is present between the threaded portion 82 and the cylindrical portion 84.

The ceramic body 90 is cap-shaped and/or sleeve-shaped and has an axial hole 91 open at the lower end of the body 90, and closed at the upper end by a cover portion of the body 90 consisting of ceramic material. The mouth portion of the axial hole 91 is formed by a conical bearing surface 92 tapering upward from the lower end of the body 90. When the device 75 is assembled, this bearing surface 92 forms with the axis 3 the same angle as the shoulder surface 22 and lies without a gap at least on the inner area thereof.

Following the conical bearing surface 92, in the upward direction, there are a cylindrical inner surface 93 and a conical inner surface 94. These inner surfaces 93, 94 surround the generally cylindrical head portion 25 and conical head portion 27, respectively, there being at most a very slight play present in particular between the conical head portion and the conical inner surface 94. Contiguous with the conical inner surface 94 there is an annular inner surface 95 which is radial and at right angles to the axis 3 and which lies opposite the end face 31 of the implant 1 at a small distance. Contiguous with the inner end of the radial inner surface 95 there is a cylindrical inner surface 96 which surrounds the cylindrical portion 84 of the bolt 80 with at most slight play. The upper end of the hole 91 is formed by an end surface 97 which is for the most part plane and which lies opposite the end surface of the bolt at a distance. The cap-shaped ceramic body 90 has a conical peripheral surface 98 which is generally rotationally symmetrical with respect to the axis 3, namely an upwardly tapering peripheral surface, but is provided with a number of recesses 99 which are distributed along the periphery and into which a turning tool can engage. At the upper end, the body 90 has an end face which is substantially, i.e. apart from the recesses 99, rotationally symmetrical, and is also smooth, plane and free from holes.

The outer edge of the conical bearing surface 92 of the ceramic body 90 has, for example, a smaller diameter than the outer edge of the shoulder surface 22, so that the latter has an area still surrounding the lower edge of the ceramic body 90. The crown 110 is made, for example, of a gold alloy and/or of porcelain and, in the finished device, fits securely on the cap-shaped ceramic body 90. The crown lies on the outer area of the shoulder surface 22 and merges steplessly and smoothly with the upper end of the peripheral surface of the trumpet-shaped portion 13 of the implant. In the uppermost cylindrical portion of the hole 91, the cap-shaped ceramic body 90 is connected nonreleasably to the cylindrical portion 84 of the bolt 80 by means of a binder 120, for example a relatively viscous cement which can be applied in a thick layer. The cement then fills the annular grooves 85 and the interspace between the upper end of the bolt 80 and the end surface 97 of the hole 91. Depending on the radial play, cement can also be present between the annular cylindrical peripheral surface portions of the cylindrical portion 84 of the bolt and the cylindrical inner surface 96 of the body 90. It should also be noted that the binder has not been shown in FIG. 4. After the binder 120 or cement has set, the bolt 80 and the cap-shaped ceramic body 90 together form a rigid indivisible unit 122.

The metal main body 50, the metal bolt 80 and the two ceramic bodies 60 and 90 are manufactured at a production station. There, the two ceramic bodies 60 and 90 are connected nonreleasably and rigidly to the main body 50 and bolt 80, respectively, by means of the binder already mentioned. The implant 1, consisting of the main body 50 and of the ceramic body 60, and the unit 122, consisting of the bolt 80 and ceramic body 90, are then supplied as two units, for example to a dental practice or dental clinic.

A dentist can insert the implant 1 according to FIG. 3 transgingivally into the mouth of a patient so that the anchoring part 5 of the implant 1 is to a large extent anchored in a hole in the bone 71, and the upper end portion of the implant 1 protrudes from the bone. The ceramic body 60 secured on the main body 50 extends approximately from the ridge of the bone 71 to about the ridge of the soft tissue. The dentist can then first secure a cap-shaped incorporation element onto the implant 1 using a screw, until the operating wound has healed. After the incorporation phase, the dentist can remove the incorporation element and can secure the unit 122, consisting of the bolt 80 and of the ceramic body 90, on the implant 1. To do this, the dentist can engage a turning tool in the recesses 99 of the ceramic body 90 and screw the threaded portion 82 of the bolt 80 into the internal thread 38 of the implant 1 until the bearing surface 92 of the ceramic body 90 lies without gaps on the shoulder surface 22 of the implant. In the finished device, the lower end portion of the cylindrical portion 84 of the bolt 80 protrudes slightly into the cylindrical hole portion 37 of the implant 1, with at most slight radial play. The unit 122 consisting of the bolt 80 and of the ceramic body 90 is then connected releasably but firmly to the implant 1 by the bolt.

Before screwing the bolt 80 into the implant 1, the dentist can, if appropriate, apply a binder 125 which additionally connects the ceramic body 90 to the peripheral surface 30 and the end face 31 of the head 7 and at least partially fills the grooves 33 of the head 7 and the interspace between the end face 31 of the head and the radial inner surface 95 of the body 90. This binder 125 consists, for example, of a temporary cement, which is used by dentists for provisionally securing temporarily fitted abutment parts and which affords a fairly secure connection, but makes it possible to once again separate the connected parts by means of a certain force. However, the binder 125 can also consist of a normal cement intended for a permanent and nonreleasable connection. The binder 125 in any case present provides, as an addition to the bolt 80 which has been screwed into the implant and which is itself releasable, a connection between ceramic body 90 and implant 1 which cannot be released at all or can only be released by means of a certain force. After their releasable or nonreleasable connection, the implant 1 and the unit 122 consisting of the bolt 80 and of the ceramic body 90 together form a stable, rigid support. To create this support, the dentist therefore only has to join together two separate units made available to the dentist, namely the implant 1 and the unit 122, within the patient's mouth. This simplifies creation of a dental prosthesis in the mouth of a patient.

When the cap-shaped ceramic body 90 is secured on the implant 1, the dentist, in order to create a dental prosthesis, can take an impression of the upper implant part and of the body 90, have the crown 110 prepared, and secure the crown on the ceramic body 90 and possibly on the shoulder surface 11 with cement (not shown). If necessary, the dentist can further grind the ceramic body 60 and/or the ceramic body 90 in places within the patient's mouth in order to optimize the shape of the dental prosthesis. To do this, for example, the areas 65 and 105 of the two originally rotationally symmetrical bodies 60 and 90, respectively, can be ground away, as indicated by dot-and-dash lines in FIGS. 2, 3 and 4. Since the end portion of the ceramic body 90 directed away from the shoulder surface 22 covers the upper end of the bolt 80 protruding from the implant 1, part of the ceramic material covering the upper bolt end can also be ground away if necessary.

The bolt 80 is laterally supported both in the internal thread 38 and in the cylindrical hole portion 37 of the implant 1. The cap-shaped ceramic body 90 is held and laterally supported by the cylindrical portion 84 of the bolt. Moreover, the body 90 lies without play and without gaps on the shoulder surface 22 of the implant and is also laterally supported by the head 7, in particular by the conical head portion 27 as far as the upper, second end 9 of the implant 1. The abutment element 77 can therefore transmit to the implant not only approximately axial forces, but also substantial forces directed approximately transverse to the axis 3, without these forces causing it to execute movements relative to the implant. This ensures substantial stability of the created dental prosthesis.

In the finished device, the soft tissue 73 adjoining the dental prosthesis lies, after incorporation, at least for the most part on the peripheral surface of the annular ceramic body 60 and has in practice grown onto the latter. It is also possible that soft tissue will lie on the crown 110, consisting for example of porcelain. By contrast, nowhere, or at least almost nowhere, does the soft tissue lie on a metal surface of the implant. This eliminates inflammations of the soft tissue. If the crown 110 is made of porcelain, the ceramic body 90 permits creation of a bright crown corresponding in color to an attractive natural tooth. If the crown 110 is made of a metal, it is electrically insulated from the metal main body 50 of the implant by the two ceramic bodies 60 and 90, so that no galvanically generated electrical current can flow from the crown 110 to the implant 1.

The ceramic body 90 indicated in FIG. 3 by solid lines, and also shown in FIG. 4, can be replaced by the ceramic body 90 indicated by dot-and-dash lines. The latter is in the main approximately cylindrical and at its lower end has an annular bearing surface whose external diameter is approximately equal to or equal to the external diameter of the shoulder surface 22.

The implant 1 of the device shown in FIG. 5 is designed in the same way as the implant shown in FIGS. 1 and 3. However, the device shown in FIG. 5 has, instead of the bolt 80, an occlusal screw 180 and, instead of the ceramic body 90, a metal body 190. The screw 180 has a threaded portion 182 and a head 183 with a polygonal hole, for example a hexagonal hole. The metal body 190 is cap-shaped and/or sleeve-shaped but has, instead of an axial blind hole, a continuous axial hole 191. The latter is stepped and at the very bottom has a conical bearing surface 192 which, as far as the outer edge of the conical shoulder surface 22 of the implant, lies on the shoulder surface. The body 190 moreover has a conical inner surface 194 which surrounds the conical head portion 27 of the implant 1 with at most slight play. The hole 191 moreover has a bearing surface 196 which widens conically upward and on which the head of the occlusal screw lies via a conical surface. The abutment element of the device shown in FIG. 5 again has a crown 110. This is cast onto the head 190 and, like the abutment element according to FIG. 3, is for example made generally of porcelain or a gold alloy. The metal body 190 has an outer surface portion which extends upward away from the outer edge of the bearing surface 192 and which merges smoothly and continuously with the outer surface of the ceramic body 60 and with which the outer surface of the crown then merges smoothly and continuously.

Above the head 183 of the occlusal screw 180, the crown 110 has a cylindrical area 132, indicated by dot-and-dash lines. This area 132 consists for example of a hole which, after insertion of the screw 180, is closed off with an insert and/or cement or the like and, if necessary, can later be exposed again—for example drilled open—without damaging the rest of the crown. This makes it possible to subsequently remove the occlusal screw and to separate the crown 110 and the body 190 from the implant 1. The surface of the device contiguous with the soft tissue is again formed at least for the most part by the ceramic body 60.

The ceramic body 60 of the implant 1 shown in FIGS. 1, 3 and 5 can be replaced by the ceramic body 60 shown in FIG. 6. This differs from the previously described body 60 in that it has, at the upper end, a plane annular surface at right angles to the axis 3. In the finished implant, this annular surface is situated below the main part of the annular surface 23 formed in FIG. 1 by the main body 50 or at the same level as said annular surface 23, and forms, by itself or together with the annular surface formed by the main body 50, a shoulder surface 22 at right angles to the axis 3.

Instead of the peripheral surface inclined outward toward the top, the sleeve-shaped and/or annular body 60 could in addition have a surface at least partially cylindrical or even inclined inward toward the top.

Figure 7:
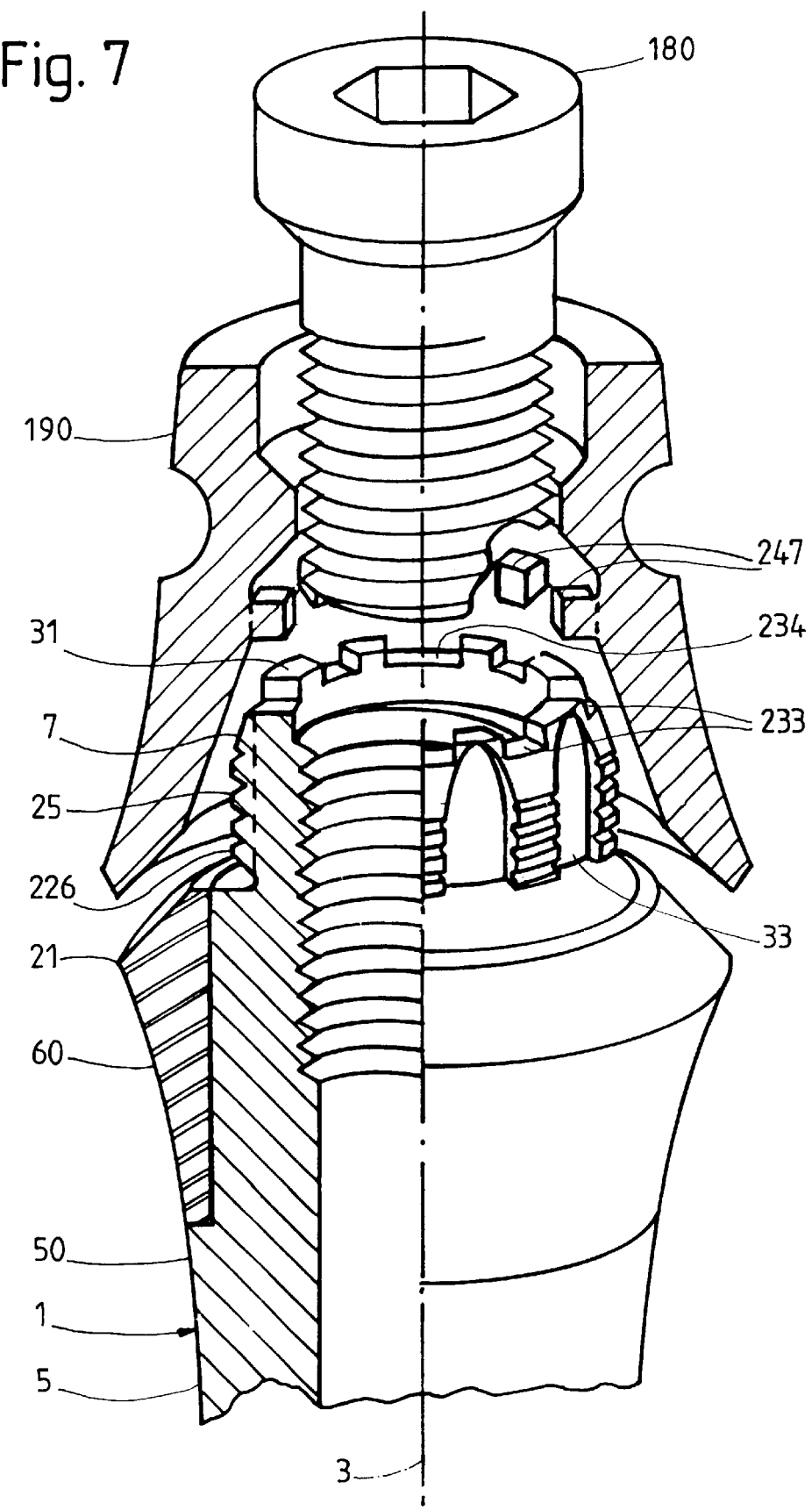
FIG. 7 shows an oblique view of another device partially cut open.

The device shown in part in FIG. 7 comprises an implant 1 whose anchoring part 5 and shoulder 21 are designed in the same way as in the implant according to FIG. 1. By contrast, the head 7 has a different design than in the implant represented in FIG. 1. The head portion 25 which is generally cylindrical and generally parallel with the axis 3 is in fact provided also with an external thread 226. Moreover, the axial grooves 33, instead of being arcuate in cross section, are for example approximately rectangular or trapezoidal. Furthermore, the annular end face 31 is provided with radial recesses or grooves 233, 234 distributed along the periphery, there being several identical first recesses or grooves 233 present, and a second, wider and/or deeper recess or groove 234. FIG. 7 also shows an occlusal screw 180 and a metal cap-shaped and/or sleeve-shaped body 190. The latter is designed similar to the body 190 represented in FIG. 5, but also has radially inwardly extending protuberances 247. These can engage in one of the first recesses or grooves 233 with at most slight play and thus position the body 190 in a rotationally fixed manner relative to the implant 1 in a position of rotation which can be selected from a number of positions of rotation.

Instead of the occlusal screw 180 and the metal body 190, however, it is possible for a metal bolt with a ceramic body secured rigidly thereon, and closed at the top, to be secured on the implant represented in FIG. 7. This bolt and ceramic body can be designed similar to the corresponding parts in FIGS. 3 and 4. The ceramic body has in particular no protuberances corresponding to the protuberances 247, so that the unit consisting of the bolt and of the ceramic body can be screwed onto the implant by turning said unit. The recesses or grooves 233 then have no positioning action. The implant shown in FIG. 7 thus optionally permits different types of securing.

Figure 8:
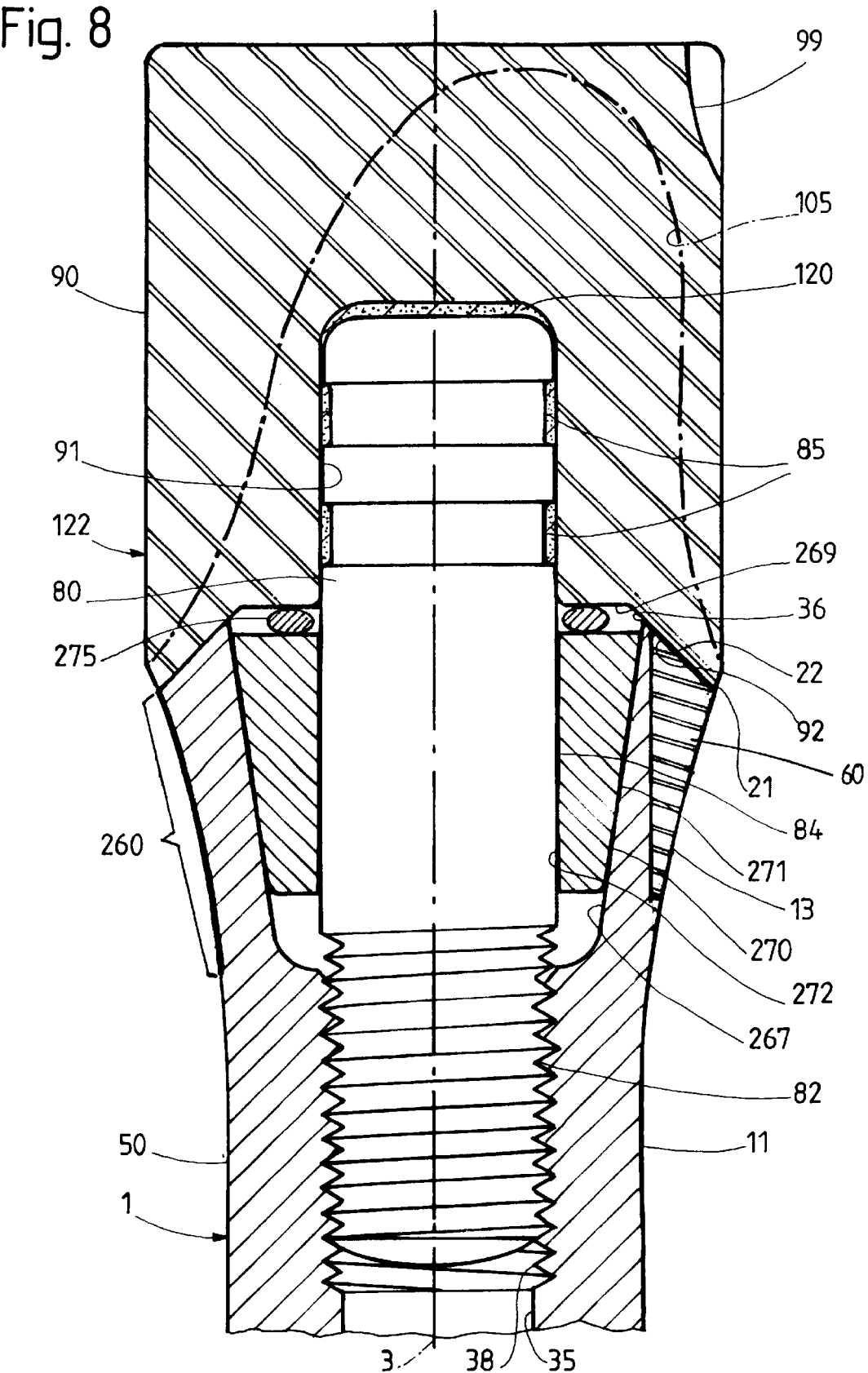
FIG. 8 shows an axial section through a further device, representing two different implant variants, one in each half.

The device shown in part in FIG. 8 comprises an implant 1 which can be designed in accordance with the left-hand half or right-hand half of the figure. From the lower end of the anchoring part 5 to the shoulder 21, both implant variants represented in half in FIG. 8 have approximately the same outer shape as the implant shown in FIG. 1. Each implant shown in FIG. 8 has in particular a generally cylindrical portion 11, a trumpet-shaped portion 13, and a shoulder 21 with a conical shoulder surface 22. The implant has a metal main body 50 which, in the variant shown in the left-hand half of the figure, also forms at least the greater part of the trumpet-shaped portion 13 and of the conical shoulder surface 22. In the variant shown on the left, the portion of the peripheral surface of the metal main body 50 extending from the outer edge of the shoulder surface 22 to near the lower end of the trumpet-shaped portion 13 is provided with a sprayed-on ceramic covering 260 which, for example, is approximately 50 μm thick. The variant of the implant shown on the right-hand half of FIG. 8 has, like the implant according to FIGS. 1 and 3, an annular and/or sleeve-shaped ceramic body 60, which forms at least the outermost part and the outer edge of the conical shoulder surface 22, for example the greater part of this, or even the whole conical shoulder surface 22. The implant shown in FIG. 8 has no head corresponding to the head 7 of the implant represented in FIG. 1. The axial blind hole 35 has a mouth 36 formed by the inner edge of the conical shoulder surface 22. Moreover, between its internal thread 38 and its mouth 36, the blind hole 35 has a conical hole portion 267 widening toward said mouth.

The device shown in FIG. 8 also comprises a metal bolt 80 and a sleeve-shaped and/or cap-shaped ceramic body 90. The bolt 80 and the body 90 are also shown in FIG. 9. The bolt 80 has a threaded portion 82 and a cylindrical portion 84. The latter is provided with annular grooves 85 near its end directed away from the threaded portion, while its area contiguous with the threaded portion is grooveless and has a smooth cylinder surface. The ceramic body 90 represented in FIG. 8 again has an axial hole 91 which is open at the bottom, closed at the top and for the most part cylindrical, and a conical bearing surface 92 which, when the device is assembled, rests on the shoulder surface 22. A plane annular surface 269 at right angles to the axis 3 adjoins the inner edge of the conical bearing surface 92. The outer edge of the bearing surface 92 has approximately or exactly the same diameter as the outer edge of the shoulder surface 22. The peripheral surface of the body 90 has, at the very bottom, an annular narrow portion which widens toward the top and which merges at least approximately continuously with that peripheral surface portion of the implant formed by the covering 260. The upper, greatest part of the peripheral surface of the body 90 is cylindrical. At the upper end of the body 90, a number of recesses 99 are present for engagement with a turning tool. As in the illustrative embodiment represented in FIG. 3, the upper end portion of the bolt 80 protrudes into the hole 91 of the ceramic body 90 and is connected nonreleasably to the body 90 by means of a binder 120, namely cement. The device according to FIG. 8 moreover has a metal ring 270, also shown separately in FIG. 10. When the device is assembled, this ring 270 is situated in the conical hole portion 267 of the implant, surrounds the cylindrical portion 84 of the bolt 80 and has a conical outer surface 271 and a cylindrical inner surface 272. The conical inner surface of the hole portion 267 and the conical outer surface 271 form, with the axis 3, the same angle, preferably 5° to 10° and for example approximately 8°. The ring is divided into somewhat resilient segments by incisions 273 shown in FIG. 10 and cut in alternately from below and from above. A deformable pressure ring 275 is arranged between the annular surface 269 of the ceramic body 90 and the plane, upper end surface of the ring 270. This pressure ring 275 consists, for example, of a soft deformable metal, for instance gold, or of an elastic or even rubber-elastic synthetic material and has the purpose of pressing the ring 270 as deep as possible into the hole portion 267 when the device is assembled.

The bolt 80 is again connected nonreleasably to the ceramic body 90 at the production site, by means of the binder 120 shown in FIG. 8, but not in FIG. 9, so that the bolt 80 and the body 90 together form a fixed unit 122. The pressure ring 275 and the ring 270 can likewise be pushed onto the bolt 80, at the production site, with the ring 270 clamped lightly on the bolt, but still displaceable along the latter. The implant 1 and the unit 122 with the rings 271 and 275 fitted on the bolt 80 are supplied, for example, to a dentist. This dentist can then insert the implant 1 transgingivally into the mouth of a patient. After incorporation of the implant 1, the dentist can connect the unit 122 with the two rings 271, 275 to the implant 1, i.e. screw the bolt 80 into the implant. When the bearing surface 92 of the body lies on the shoulder surface 22, the deformable pressure ring 275 presses the ring 270 downward, so that the latter bears firmly, and practically free from play, with its outer surface 271 on the inner surface of the conical widening 267 and with its inner surface 272 on the cylindrical surface of the bolt 80. The ring 271 thus centers the bolt and supports it laterally in the implant between the internal thread 38 and the mouth 36 of the blind hole 35, almost as far as the mouth 36. The implant 1 and the unit 122 then together form a stable support. After inserting the unit 122 into the mouth of the patient, the dentist can, if necessary, grind away at least an area 105 of the ceramic body 90 and attach a crown or other superstructure thereon. That surface of the dental prosthesis contiguous with the soft tissue is then formed at least for the most part by the peripheral surface of the ceramic covering 260 and possibly also by a portion of the peripheral surface of the ceramic body 90.

Figure 11:
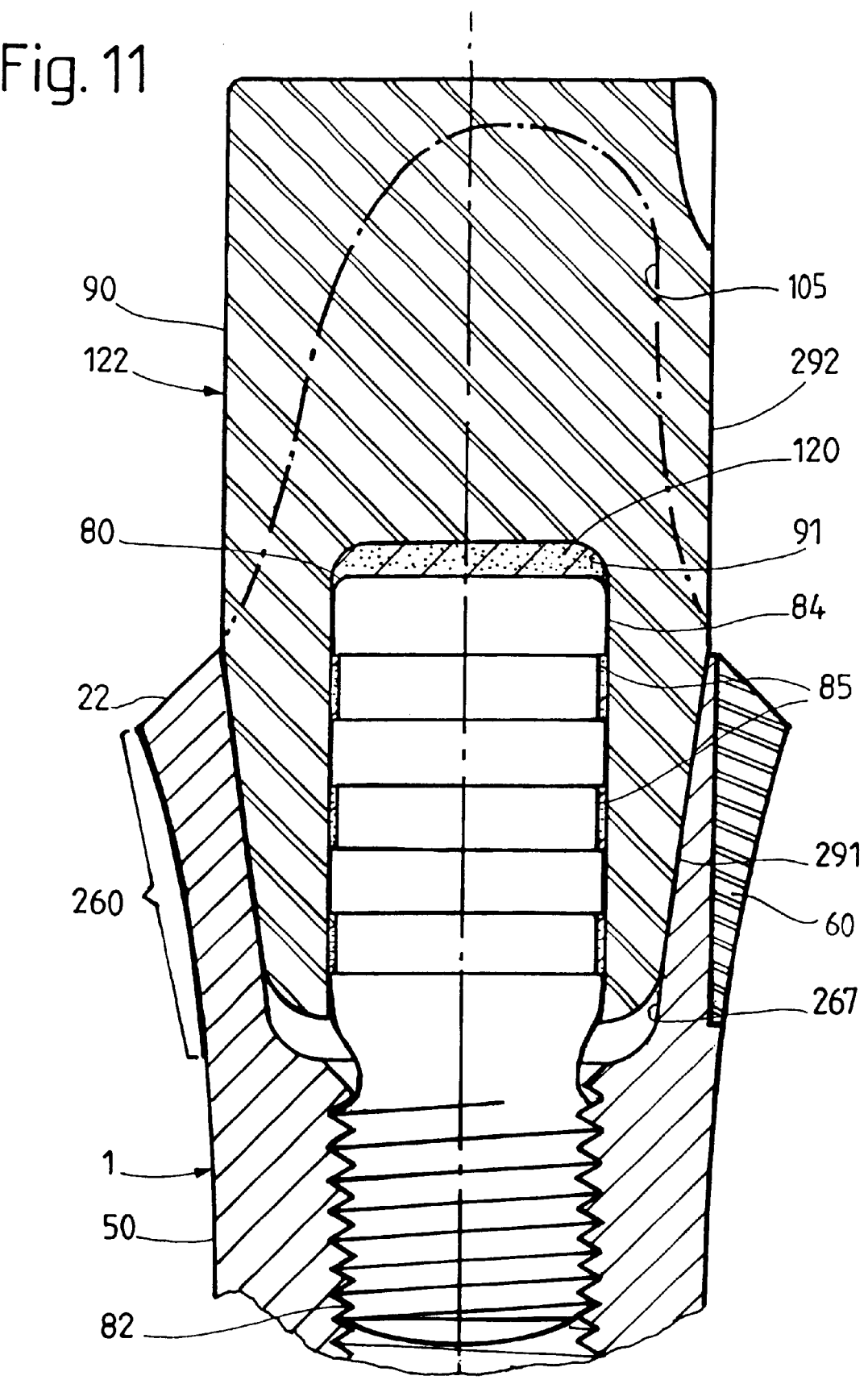
FIG. 11 shows an axial section through a device with the same implant variants as in FIG. 8.

The device shown in part in FIG. 11 comprises an implant 1 designed according either to the left-hand half or right-hand half of the figure. The two implant variants each shown in half are designed in the same way as the implant variants shown in FIG. 8 and have a metal main body 50 and a ceramic covering 260 or body 60, respectively. The device according to FIG. 11 also has a unit 122, represented separately in FIG. 12, with a metal bolt 80 and a ceramic body 90. The bolt has a threaded portion 82 and a cylindrical portion 84 and is similar to the bolt shown in FIG. 3, but protrudes at most slightly from the implant, when the device is assembled, and, in the cylindrical portion 84, has for example three instead of two annular grooves 85. The ceramic body 90 shown in FIGS. 11 and 12 has a conical portion 291 which tapers toward the lower end of the body 90 and, when the device is assembled, sits firmly and free from play in the conical hole portion 267 of the implant. The body 90 also has a generally cylindrical portion 292 which, when the device is assembled, is situated above the implant 1. In contrast to the body 90 according to FIG. 8, the body 90 of the device represented in FIG. 11 does not lie on the shoulder surface 22, but is surrounded by the latter.

The bolt 80 again protrudes into an axial hole 91, closed at the top, of the body 90 and is connected to it by a binder 120. After the implant has been inserted into a bone, a dentist can screw the unit 122 into the implant. The conical portion 291 then lies free from play and firmly on the inner surface of the conical hole portion 267 and is supported radially and also axially by the latter. The cone surfaces bearing on each other further provide inhibition and a clamping action, so that in practice the unit 122 cannot inadvertently come loose. Moreover, the conical portion 291 of the body 90 could additionally be secured in the hole portion 267 with a binder. If necessary, the cylindrical portion 292 of the ceramic body 90 can be ground so that it acquires, for example, the shape shown by dot-and-dash lines in FIG. 11, and the area 105 is ground away. A crown (not shown) bearing on the shoulder surface 22 can be secured for example on the conical portion 292.

Figure 13:
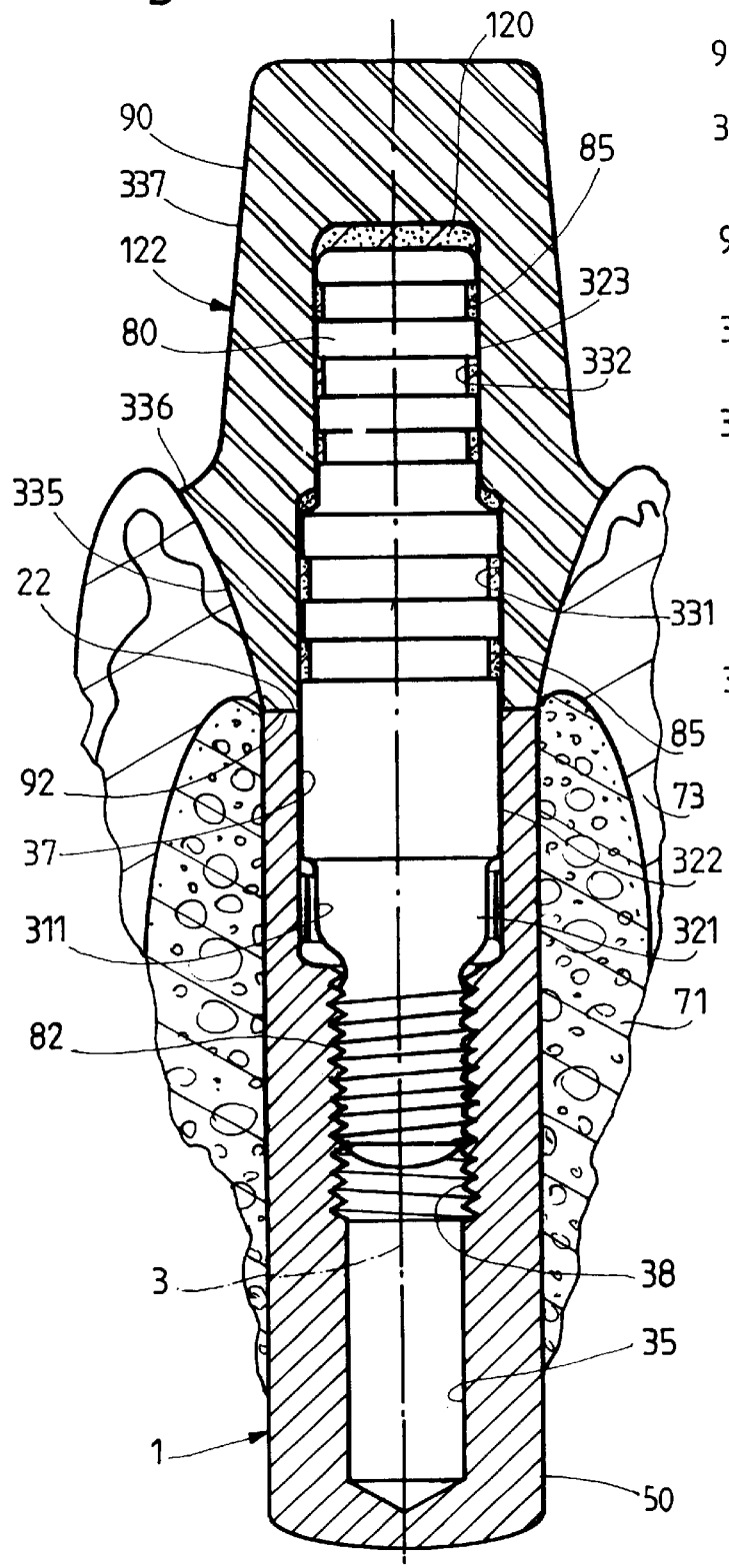
FIG. 13 shows an axial section through a device.

The device shown in part in FIG. 13 comprises an implant 1. The latter consists exclusively of a one-piece metal main body 50. The latter is cylindrical as far as its upper, second end, but if appropriate it can also have an external thread (not shown). At the upper end, the implant has an annular, plane shoulder surface 22 at right angles to the axis 3 and does not have a head protruding above the shoulder surface. The axial blind hole 35 of the implant has a mouth formed by the inner edge of the shoulder surface 22, adjoining this a cylindrical hole portion 37, and, further down, an internal thread 38. The diameter of the cylindrical portion 37 is distinctly greater than the maximum diameter or nominal diameter of the internal thread 38. Between the cylindrical portion 37 and the internal thread 38 there is a hole portion 311 which comprises inwardly extending protuberances distributed along the periphery and, between these, interspaces which form axial grooves.

The device according to FIG. 13 again comprises a unit 122 with a metal bolt 80 and a ceramic body 90 connected to the latter by a binder 120. In this variant, the bolt 80 has a threaded portion 82 and, extending away from this in succession, a first cylindrical bolt portion 321, a second cylindrical bolt portion 322 and a third cylindrical bolt portion 323. The second cylindrical bolt portion 322 has a greater diameter than the other two cylindrical portions 321, 323. The upper area of the second cylindrical portion 322 and the third cylindrical portion 323 are provided with annular grooves 85.

Figure 14:
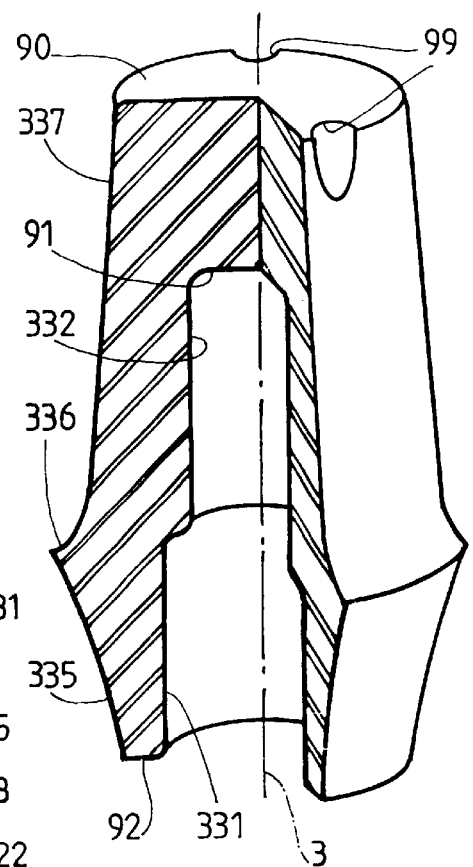
FIG. 14 shows the ceramic body of the device according to FIG. 13, cut open and in an oblique view.

The ceramic body 90 shown in FIG. 13, and also represented separately in FIG. 14, has an axial hole 91, again closed at the top. This hole 91 has a further cylindrical hole portion 331 adjoining its mouth, and a narrower cylindrical hole portion 332. That area of the cylindrical portion 322 comprising annular grooves and the cylindrical portion 323 of the bolt fit with at most slight radial play in the hole portions 331 and 332, respectively, of the ceramic body 90 and are connected to the body 90 by the binder 120. When the device is assembled, the ceramic body 90 lies with its plane bearing surface 92, at right angles to the axis 3, on the shoulder surface 22 of the implant, the two surfaces 22, 92 having the same external diameter and the same internal diameter. That portion 331 of the body 90 contiguous with the bearing surface 92 has a peripheral surface which is slightly concavely curved in axial section and widens toward the top in a trumpet shape and which, when the device is assembled, merges at least approximately continuously with the cylindrical peripheral surface of the implant 1. The upper end of the trumpet-shaped portion 335 is connected, via a shoulder surface 336 which is concavely curved and/or conical in axial section, to a conical portion 337 tapering upward. This conical portion 337 is provided with a number of recesses 99.

In use, the implant 1 is inserted subgingivally into a bone 71 so that the shoulder surface 22 is situated approximately level with the bone ridge below the soft tissue 73, but is accessible from around the bone when the soft tissue is cut open. After the implant has become incorporated, the bolt 80 of the unit 122 is screwed into the implant. The lower part of the second cylindrical bolt portion 322 is then guided and supported radially and approximately free from play in the cylindrical hole portion 37 of the implant, while the bolt portion 321 passes through the portion 311 of the hole with considerable play and for example without contact. If necessary, the ceramic body 90 can again be ground. Moreover, a crown (not shown) can for example be secured on the conical portion 337 of the body 90 in such a way that the crown lies on the shoulder surface 336.

Figure 15:
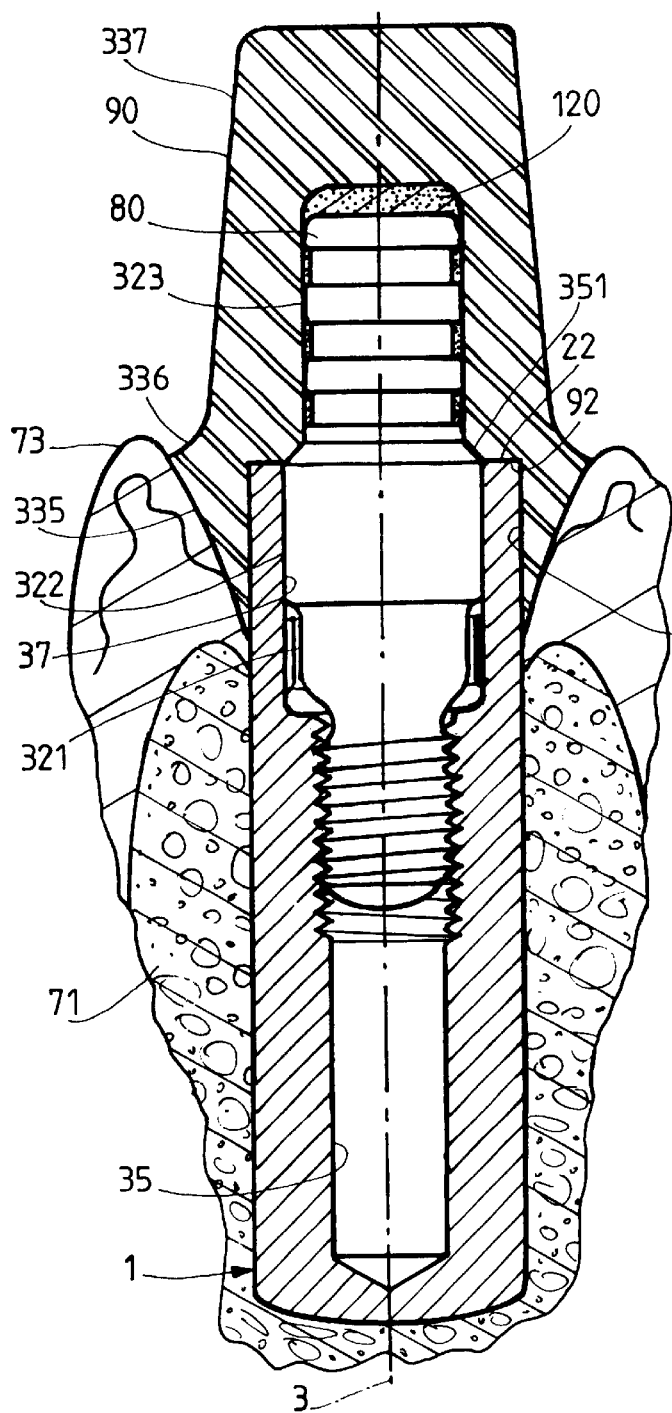
FIG. 15 shows an axial section through a device.
Figure 16:
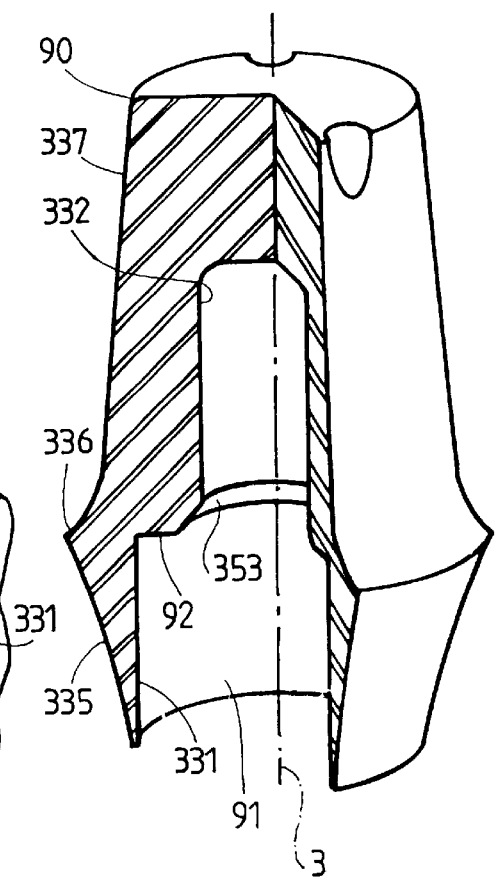
FIG. 16 shows an oblique view of the cut-open ceramic body of the device according to FIG. 15, FIGS. 17 and 18 show axial sections through different devices.

The implant 1 of the device represented in FIG. 15 is designed in the same way as the implant according to FIG. 13. The bolt 80 of the unit 122 shown in FIG. 15 has, like the bolt shown in FIG. 13, a threaded portion 82 and three cylindrical bolt portions 321, 322, 323, the second cylindrical bolt portion 322 however being shorter, having no annular grooves and being connected to the cylindrical portion 323 via a short conical bolt portion 351. The ceramic body 90 of the unit 122 shown in FIG. 15 is also represented separately in FIG. 16 and has an axial hole 91 with two cylindrical hole portions 331, 332. Between the wider hole portion 331, adjoining the mouth of the hole 91, and the narrower hole portion 332, there are an annular plane bearing surface 92, at right angles to the axis 3, and an upwardly tapering, conical hole portion 353. Like the body shown in FIGS. 13 and 14, the body 90 shown in FIGS. 15 and 16 has an upwardly widening trumpet-shaped portion 335, a shoulder surface 336 and a conical portion 337. The outer edge of the shoulder surface 336 is situated approximately level with the bearing surface 92. The cylindrical bolt portion 323 and the conical bolt portion 351 of the bolt fit in the cylindrical hole portion 332 and in the conical hole portion 353, respectively, of the body 90, the bolt again being connected to the body 90 by a binder 120.

The implant 1 shown in FIG. 15 is inserted transgingivally so that the shoulder surface 22 of the implant is situated above the bone 71 approximately level with the ridge of the soft tissue 73. When the bolt 80 is screwed into the blind hole 35 of the implant, the second cylindrical bolt portion 322 is situated completely in the cylindrical hole portion 37 of the implant and is approximately flush with the mouth of the hole 35. The ceramic body 90 then lies with its bearing surface 92 on the shoulder surface 22 of the implant. The upper end portion of the implant 1 fits with at most slight radial play in the cylindrical hole portion 331 of the body 90 and can, if appropriate, be connected to the body 90 by an adhesive which can be applied in a thin layer. The peripheral surface, slightly concavely curved in axial section, of the portion 335 of the ceramic body 90 merges at the lower end of said body 90 almost steplessly into the cylindrical peripheral surface of the implant. That surface of the device contiguous with the soft tissue 73 is formed at least for the most part by the peripheral surface of the portion 335 of the ceramic body 90.

The device represented in FIG. 17 has an implant 1 with a metal main body which consists of two one-piece parts connected releasably to each other, namely a generally cylindrical body 360 and an intermediate bolt 370 which is screwed into the latter. An annular and/or sleeve-shaped ceramic body 60 is held on the intermediate bolt 370. Screwed into the intermediate bolt 370 is another bolt which, like the bolt shown for example in FIGS. 3 and 4, is designated by 80. A ceramic body is secured on the bolt 80, which ceramic body is cap-shaped and closed at the top and, like the cap-shaped ceramic body according to FIGS. 3 and 4, is designated by 90. The generally cylindrical body 360 is designed similarly to the one-piece main body 50 according to FIG. 13. However, the blind hole of the body 360 has, between the internal thread 38 and the hole portion 311 comprising protuberances and interspaces, a threadless cylindrical diameter of the internal thread or slightly greater than this and smaller than the diameter of the cylindrical hole portion 37 adjoining the mouth of the blind hole 35. The intermediate bolt 370 has a threaded portion 371 screwed into the internal thread 38, two cylindrical bolt portions 372 and 373 guided in the hole portions 361 and 37, respectively, a flange 374, and, protruding upward from the latter, a cylindrical bolt portion 375. The flange 374 has at the top and bottom a plane annular surface and lies on the annular end surface of the body 360. The intermediate bolt 370 is provided with a blind hole 377 which opens into its upper end and which has an internal thread 378. In the variant shown in FIG. 17, the ceramic body 60 lies on the flange at 373 and surrounds the cylindrical bolt portion 375. The bolt 80 is screwed with its threaded part into the internal thread 378 of the intermediate bolt 370. The sleeve-shaped ceramic body 60 has, at its upper end, a plane annular surface which is for example situated slightly above the annular end surface of the bolt 370 and can be regarded as a shoulder surface of the implant 1. The cap-shaped ceramic body 90 secured nonreleasably on the bolt 80, and forming a unit 122 with the latter, lies with a plane annular bearing surface on said annular surface of the ceramic body 60 and presses the latter against the flange 374. In this variant, the sleeve-shaped ceramic body 60 can possibly be attached only to the intermediate bolt 370 and, when the device is assembled, it is then held securely on the intermediate bolt 370 by the unit 122. However, the ceramic body 60 can for example be secured nonreleasably on the intermediate bolt 370 by means of a press-fit connection and/or a binder. The metal body 360 of the implant 1 is inserted subgingivally, so that the soft tissue is contiguous with the ceramic body 60 and possibly also slightly with the ceramic body 90 and the flange 324.

The device shown in FIG. 18 comprises a generally cylindrical implant 1 with a one-piece metal main body 50 and an annular and/or sleeve-shaped ceramic body 60 secured thereon. As in the case of the main body shown in FIG. 1, the blind hole 35 has, between its mouth and its internal thread 38, a short cylindrical hole portion 37 which is at least equal to the nominal diameter or maximum diameter of the internal thread and, for example, slightly greater than the nominal diameter of the thread. At their upper ends, the metal main body 50 and the ceramic body 60 have plane annular end surfaces, that of the ceramic body 60 for example being situated slightly above the end surface of the main body and serving as a shoulder surface of the implant. The two annular end surfaces could, however, also be flush with each other.

The device according to FIG. 18 also comprises a secondary part or abutment element 390 with a head 391 and a bolt 392. The bolt 392 has a threaded portion screwed into the internal thread 38 radially supported and approximately free from play in the hole portion 37. The head 391 lies with an annular plane bearing surface free from gaps on the upper end surface of the ceramic body 60. The latter can be attached and held securely on the main body 50 by the abutment element 390 or secured nonreleasably on the main body by means of a press-fit connection and/or a binder. The head 391 is for example conical and has a blind hole opening into its upper end and with an internal thread. The implant 1 is inserted transgingivally in a patient's mouth. The device according to FIG. 18 serves, together with at least one other similar device and/or possibly a natural tooth, for holding and/or creating a bar construction, where a bar (not shown) can be secured on the head 391.

The implant 1 represented in FIGS. 19 and 20 is designed similarly to the implant 1 and comprises a one-piece metal main body 50 and, secured thereon, an annular and/or sleeve-shaped ceramic body 60. As in the implant according to FIG. 1, this ceramic body 60 forms the conical shoulder surface 22 of the implant. However, on its end face at the upper inner edge of the conical shoulder surface 22, the ceramic body 60 also has a relatively wide, annular and for the most part plane end face 401. The latter is provided with an axially extending protuberance 402 or cam 402, it being possible for a plurality of protuberances 402 to be distributed uniformly along the periphery of the annular surface around the axis 3.

The unit 122 shown in FIG. 20 can for example be secured on the implant 1 shown in FIGS. 19 and 20, said unit 122 having a bolt 80 and a ceramic body 90 secured thereon. The bolt 80 and the ceramic body 90 are designed similar to FIG. 3. When the device is assembled, the ceramic body 90 lies in particular with an annular conical bearing surface 92 on the conical shoulder surface 22. However, the body 90 shown in FIG. 20 comprises, inside of the conical bearing surface 92, an annular groove 405 into which the protuberance or protuberances 402 protrude with play when the device is assembled. The groove 405 makes it possible to screw the unit 122 securely on the implant by turning, without obstruction by the protuberance 402 or protuberances 402.

The cap-shaped body 410 shown in part in FIG. 21, and preferably made of metal, for example gold or a gold alloy, can be secured on the implant according to FIGS. 19 and 20 instead of the unit 122 shown in FIG. 20. The body 410 is designed in a similar way to the body 190 shown in FIG. 5 and like this has a continuous axial hole 411, so that, like the body 190, it can be secured on the implant with an occlusal screw. The body 410 has an annular, generally conical bearing surface 412 which at least in part lies on the conical shoulder surface 22 of the implant 1 when the body 410 is secured thereon. The bearing surface 412 is provided with several, for example twelve, recesses 413 distributed uniformly along the bearing surface. When the body 410 is secured on the implant according to FIG. 19, the or each protuberance 402 protrudes into a recess 413 and secures the body 410 against rotation. The body 410 can thus alternately be positioned in a rotationally fixed manner in one of several positions of rotation relative to the implant 1.

The device shown in FIG. 22 is designed similarly to the device according to FIG. 20. However, the ceramic body 60 shown in FIG. 22 comprises, instead of a conical shoulder surface, a plane annular shoulder surface 22 adjoined on the inside by an annular step 423 with a steep, slightly conical or cylindrical flank, and a plane annular surface provided with at least one protuberance 402. The ceramic body 90 is designed in such a way that it lies, free from gaps, with an annular plane bearing surface on the plane shoulder surface 22.

The implant 1 represented in FIG. 23 has a similar outline shape to the implant according to FIGS. 19 and 20, but comprises a main body 50 which is formed by two originally separate parts, namely a primary part 431 and a secondary part 432. The latter has a bolt which is screwed into a blind hole of the primary part, and a portion which protrudes from the primary part and forms the head 7 of the implant 1. The ceramic body 60 secured on the primary part 431 forms the shoulder surface 22 of the implant and has two or more protuberances 402 or cams 402 distributed along its periphery.

The implant represented in FIG. 24 has, like the implant according to FIG. 23, a metal main body 50 consisting of a primary part 431 and of a secondary part 432. On its end face, the ceramic body 60 secured on the primary part 431 has, instead of protuberances 402, at least one recess 432 and, for example, two or more recesses 432 distributed along the periphery. Each recess 432 consists of a groove which is radial with respect to the axis 3. On the implant designed according to FIG. 24, it is possible alternately to secure a unit with a bolt and a ceramic body not engaging in the recesses, or a metal cap-shaped body which has at least one protuberance engaging in a recess 432 and is thereby positioned in a rotationally fixed manner.

It should also be noted that at least the outermost annular area of the shoulder surfaces 22 formed by the ceramic bodies 60 in all the implants represented in FIGS. 19, 20, and 22 to 24, is continuously smooth along the entire periphery and is either conical or plane. Despite the protuberances or recesses along the entire periphery of the shoulder surfaces, the bodies secured on these implants can therefore lie on these in a manner free from gaps. The protuberances 402 and recesses 433 of the ceramic bodies 60 are situated on an annular area which is coaxial to the axis 3 and surrounds the head of the implant in axial projection. The protuberances 402 and recesses 433 therefore have a relatively large radial distance from the axis 3. This contributes to exact positioning and stable rotational securing of bodies which are secured on the implants and engage with the protuberances and recesses.

Moreover, a ceramic body with a plane annular shoulder surface secured on a one-piece or two-piece metal main body can also be provided with at least one protuberance or at least one recess. The protuberances or recesses can then extend, for example, in radial direction only over the inner part of the shoulder surface, so that on the outside the shoulder surface has a smooth, plane portion along the whole of the periphery.

The ceramic bodies 60 of the implants according to FIGS. 19 to 24 and of the implant variants described in the preceding paragraph can, like the implant according to FIG. 7, have several identical first protuberances or recesses and an otherwise dimensioned second protuberance or an otherwise dimensioned second recess. For example, several identical first protuberances and a narrower and/or lower second protuberance, or several identical first recesses and a second wider and/or deeper recess can be provided. The bodies which can be secured on the implant using a screw can then have recesses and/or protuberances cooperating with the protuberances and/or recesses of the ceramic bodies, such that an implant, independently of the design of the body secured on it, positions said body alternately in one of several positions of rotation or only in a single position of rotation.

The parts described with reference to FIGS. 5 to 24 can, unless otherwise stated in the description of the corresponding figures, in each case be designed similarly, and have similar properties, as in the first described illustrative embodiment and/or as in another previously described illustrative embodiment.

The devices can also be modified in different ways. In particular, features of different illustrative embodiments can be combined with one another.

A bolt 80 and the hole 91 of the ceramic body 90 secured on the bolt can have, in cross section, portions which are not rotationally symmetrical with respect to the axis and which fit into each other with at most slight play. Said portions can, for example, be polygonal or have at least one plane surface which is parallel with the axis or forms, with the latter, an angle other than 90°. In this way, the ceramic body 90 is positioned nonrotationally on the bolt and is additionally secured against turning relative to the bolt.

Like a natural tooth root, the anchoring part of the implant can also taper at least approximately along its entire height toward the lower, first end of the implant, but for example can also have an external thread, so that, after extraction of a tooth, the implant can be inserted immediately into the bone.

Moreover, the implants shown in the various figures can also be used in combination with other abutment elements or superstructures and with other parts which serve, for example, to create individual teeth, bridges, and prostheses with a plurality of artificial teeth.

What is claimed is:

1. A device for at least one of holding and forming a dental prosthesis, the device comprising:

an implant formed of a metal main body and adapted to be at least partially anchored in a bone, said metal main body having an axis, a first implant end intended to be inserted into the bone, and a second implant end intended to protrude from the bone;

an annular ceramic body secured to the metal main body and having an end directed away from the bone, wherein the annular ceramic body secured on the metal main body has, at its said end, at least one of at least one protuberance and at least one recess, and an annular shoulder surface facing away from said first implant end and forming an angle with said axis, at least an annular area of said shoulder surface encompasses said axis and said at least one of at least one protuberance and of at least one recess and is continuously smooth all around the axis; and a body attachable to the implant at said second implant end and having an annular bearing surface which lies on said annular area of the shoulder surface when said body is attached to the implant.

2. The device according to claim 1, wherein the metal main body has a head which protrudes away from the annular shoulder surface and from the at least one of at least one protuberance and at least one recess, said head having a generally conical head portion tapering away from the annular shoulder surface, and wherein said generally conical head portion, when the body attachable to the implant lies on the annular shoulder surface, supports said body, with at most slight radial play at a conical inner surface of said body.

3. The device according to claim 2, wherein the shoulder surface is conical, tapering toward the head and has an inner edge, the head has a maximum diameter which is smaller than a diameter of the inner edge of the conical shoulder surface and the generally conical head portion extends substantially to the second implant end and has a conical enveloping surface forming with the axis an angle which is smaller than an angle formed by the conical shoulder surface with the axis.

4. The device according to claim 2, wherein the generally conical head portion has a conical enveloping surface which forms with the axis an angle in the range of approximately 15° to approximately 25°.

5. The device according to claim 2, wherein the head is one of formed of a one-piece part including the metal main body and of a secondary part screwed into a threaded bore of the metal main body.

6. The device according to claim 2, wherein the head comprises a head portion which is generally parallel with said axis and disposed between the shoulder and the generally conical head portion, said body attachable to the implant comprises an end portion forming said annular bearing surface and extending, when said body is attached to the implant, along said axis from an outermost edge of said annular bearing surface to said conical inner surface and said end portion of the body lies a distance outside the conical inner surface.

7. The device according to claim 1, wherein the metal main body has an axial hole formed in said second implant end, a wall of said second implant end surrounding the axial hole having an internal thread and wherein said body is attached to the implant by one of a bolt having an external thread screwed into said internal thread of the metal main body and protruding into a hole of said body and being rigidly secured to said body, and of a screw which engages said body attachable to the implant and is screwed into said internal thread of the metal main body.

8. The device according to claim 1, wherein said body attachable to the implant and comprising said annular bearing surface is made from ceramic material.

9. The device according to claim 8, wherein said body is attachable to the implant by means of a bolt which protrudes into a blind hole of said body and is rigidly connected thereto.

10. The device according to claim 1, wherein at least one of said at least one protuberance projects in a generally axial direction from said annular shoulder surface and said at least one recess is cut in a generally axial direction into said annular shoulder surface.

11. The device according to claim 1, wherein the body attachable to the implant is formed in such a manner that it does not engage the at least one of at least one protuberance and at least one recess of the annular ceramic body so that the body attachable to the implant can be rotated in any rotational position with respect to the axis of the implant until it is rigidly secured to the implant.

12. The device according to claim 1, wherein the body attachable to the implant comprises an annular groove into which at least one protuberance of the ceramic body protrudes when the body attachable to the implant is attached to the implant so that the body attachable to the implant can be rotated in any rotational position with respect to the axis of the implant until it is rigidly secured to the implant.

13. The device according to claim 1, wherein the body attachable to the implant has at least one of at least one recess and at least one protuberance which engages at least one of the at least one protuberance and the at least one recess of the ceramic body when this body is attached to the implant so that this body can be attached to the implant in a rotationally fixed manner in at least one position of rotation relative to the implant.

14. The device according to claim 1, wherein the body attachable to the implant has several recesses which are distributed around the axis and into any of which at least one protuberance of the ceramic body can protrude when the body attachable to the implant is attached to the implant so that this body can alternately be attached in a rotationally fixed manner in one of several positions of rotation relative to the implant.

15. A device for at least one of holding and forming a dental prosthesis, the device comprising:
  an implant having an anchoring part with a first implant end adapted to be at least partially anchored in a bone, a shoulder spaced a distance from the first implant end, and a head protruding away from the shoulder forming a second implant end and adapted to protrude from the bone, said implant having an axis, and an axial hole formed in said second implant end where a wall of said second implant end surrounding the axial hole has an internal thread, said implant further having at least one of at least one protuberance and at least one recess arranged at the shoulder, wherein the shoulder has an annular shoulder surface facing away from said first implant end and forming an angle with said axis and of which at least an annular area encompasses said axis and said at least one of at least one protuberance and at least one recess and is continuously smooth all around the axis, wherein the head has a generally conical head portion tapering away from the shoulder; and
  a body comprising a conical inner surface forming a hole and being attachable to said implant by means of one of a bolt having a portion with an external thread screwed into the internal thread of the axial hole of the second implant end and a screw having an external tread screwed into the internal thread of the axial hole of the second implant end, wherein said body further includes an annular bearing surface which lies on said annular area of the shoulder surface when said body is attached to the implant and said generally conical head portion supports said body with at most slight radial play at said conical inner surface when said body is attached to the implant.

16. The device according to claim 15, wherein the shoulder surface is conical, tapering toward the head and has an inner edge, wherein the head has a maximum diameter which is smaller than a diameter of the inner edge of the conical shoulder surface and wherein the generally conical head portion extends substantially to the second implant end and has a conical enveloping surface forming with the axis an angle which is smaller than an angle formed by the conical shoulder surface with the axis.

17. The device according to claim 15, at least one of wherein said at least one protuberance projects in a general axial direction from the shoulder and wherein said at least one recess is cut in a generally axial direction into the shoulder.

18. The device according to claim 15, wherein said body attachable to the implant is formed in such a manner that it does not engage the at least one of at least one protuberance and at least one recess of the implant so that said body can be rotated in any rotational position with respect to the axis of the implant until it is rigidly secured to the implant.

19. The device according to claim 15, wherein said body attachable to the implant further comprises an annular groove into which at least one protuberance of the implant protrudes when the body is attached to the implant so that the body attachable to the implant can be rotated in any rotational position with respect to the axis of the implant until it is rigidly secured to the implant.

20. The device according to claim 15, wherein said body attachable to the implant has at least one of at least one recess and at least one protuberance which engages at least one of the at least one protuberance and the at least one recess of the implant when said body is attached to the implant so that the body can be attached to the implant in a rotationally fixed manner in at least one position of rotation relative to the implant.

21. The device according to claim 15, wherein said body attachable to the implant has several recesses which are distributed around the axis and into any of which at least one protuberance of the implant can protrude when said body is attached to the implant so that the body can alternately be positioned in a rotationally fixed manner in one of several positions of rotation relative to the implant.

22. The device according to claim 15, wherein the implant comprises a metal main body forming a major portion of said anchoring part and
  wherein the implant further comprises one of an annular ceramic body which is secured to the metal main body and forms said annular shoulder surface and said at least one of at least one protuberance and at least one recess, and a ceramic covering provided on a peripheral surface portion of the metal main body and extending from an outer edge of the annular shoulder surface toward the first implant end.

23. The device according to claim 15, wherein the implant comprises a metal main body forming at least a major portion of the anchoring part and
  wherein the head is one of formed of a one-piece part including the metal main body and of a secondary part screwed into a threaded bore of the metal main body, said secondary part forming said axial hole.

24. The device according to claim 15, wherein the head comprises a head portion which is generally parallel with said axis and disposed between the shoulder and the generally conical head portion, said body attachable to the implant comprises an end portion forming said annular bearing surface and extending, when said body is attached to the implant, along said axis from an outermost edge of said annular bearing surface to said conical inner surface and said end portion of the body lies a distance outside the conical inner surface.

25. The device according to claim 15, wherein said body being attachable to the implant is made of ceramic material.

26. The device according to claim 25, wherein said hole of said body being attachable to the implant is a blind hole with said conical inner surface facing away from the implant when said body is attached to the implant by means of a bolt which protrudes into the blind hole of said body, said conical inner surface being rigidly connected to the bolt and closed off by the ceramic material of said body.

27. A set comprising a device according to claim 15 and at least one further body which can be attached to the implant instead of the body which belongs to the device,
   wherein one of said bodies attachable to the implant is formed so that it does not engage the at least one of at least one protuberance and at least one recess of the implant so that the body attachable to the implant can be rotated in any rotational position with respect to the axis of the implant until it is rigidly secured to the implant and
   wherein another of said bodies attachable to the implant has at least one of at least one recess and at least one protuberance which engages at least one of the at least one protuberance and the at least one recess of the implant when this body is attached to the implant so that this body can be attached to the implant in a rotationally fixed manner in at least one position of rotation relative to the implant.

28. The set according to claim 27, wherein at least one protuberance of the implant projects in a generally axial direction from the shoulder and is tapering away from said first implant end in a view radial to said axis and at least one recess of said one of said bodies is tapering away from said first implant end in a view readial to said axis of the implant when said body is attached to the implant.

29. A device for at least one of holding and forming a dental prosthesis, the device comprising:
   an implant having an anchoring part with a first implant end adapted to be at least partially anchored in a bone, a shoulder spaced a distance from the first implant end, and a head protruding away from the shoulder forming a second implant end and adapted to protrude from the bone, said implant having an axis,
   wherein the shoulder has an annular conical shoulder surface facing away from said first implant end and tapering away from said first implant end and forming an angle with said axis,
   wherein the head has a first head portion which protrudes away from the shoulder and is substantially parallel with the axis of the implant and a second head portion which is generally conical, protrudes away from said first head portion toward said second implant end, tapers away from the first implant end and has a conical enveloping surface forming with said axis an angle which is smaller than an angle formed by said annular conical shoulder surface with said axis,
   wherein a major part of said anchoring part and the first implant end of said implant includes a metal main body, and
   wherein said implant further comprises one of an annular ceramic body which is secured to the metal main body and forms at least an outer portion of said annular shoulder surface and a ceramic covering provided on a peripheral surface portion of the metal main body and extending from an outer edge of the annular shoulder surface toward the first implant end; and
   a ceramic body which is adapted for supporting one of a crown of an individual artificial tooth, a part of a bridge and a part of a prosthesis with a plurality of artificial teeth, said ceramic body having a conical bearing surface forming a hole where said conical bearing surface is a conical inner surface attachable to the implant, wherein, when the ceramic body is attached to the implant, an annular bearing surface of said ceramic body lies on the annular conical shoulder surface of the implant and the second conical head portion supports the conical inner surface of the ceramic body with at most slight play.

30. The device according to claim 29, wherein the head has a maximum diameter which is smaller than a diameter of an inner edge of the annular conical shoulder surface.

31. The device according to claim 29, wherein the annular conical shoulder surface forms with the axis an angle in the range of approximately 40° to approximately 50° and the conical enveloping surface of the head forms with the axis an angle in the range of approximately 15° to approximately 25° and extends substantially to the second implant end.

32. The device according to claim 29, wherein the implant comprises an axial hole into said second implant end and an inner wall of said second implant end has an internal thread, and the device further comprises a bolt which protrudes into the hole of the ceramic body and is connected thereto, said bolt has a portion with an external thread screwed into said internal thread of the implant when said body being attachable to the implant is attached to the implant.

33. The device according to claim 32, wherein said hole formed by said conical bearing surface of said ceramic body is a blind hole, said conical bearing surface has an end directed away from the metal main body that is closed off by ceramic material of the ceramic body.

34. The device according to claim 32, wherein the implant comprises a metal main body forming a major part of the implant including the first implant end and the implant further comprises one of an annular ceramic body which is secured to the metal main body and forms at least an outer part of said annular shoulder surface and a ceramic covering provided on a peripheral surface portion of the metal main body and extending from an outer edge of the annular shoulder surface toward the first implant end.

35. The device according to claim 29, wherein said ceramic body comprises an end portion forming said annular bearing surface and extending, when said body is attached to the implant, along said axis from an outermost edge of said annular bearing surface to said conical inner surface and said end portion of the body lies a distance outside the conical inner surface.

36. A device for at least one of holding and forming a dental prosthesis, the device comprising:
   an implant having an anchoring part with a first implant end adapted to be at least partially anchored in a bone, a shoulder spaced a distance from the first implant end, and a head protruding away from the shoulder forming a second implant end and adapted to protrude from the bone, said implant having an axis, and an axial hole formed in said second implant end where an inner wall of the implant surrounding the axial hole has an internal thread, wherein the shoulder has an annular conical shoulder surface facing away and tapering away from said first implant end, wherein the head has a first head portion which protrudes away from the shoulder and is substantially parallel with the axis of the implant and second head portion which protrudes away from said first head portion toward said second implant end, is generally conical, tapers away from the first implant end and has a conical enveloping surface forming with said axis an angle which is smaller than an angle formed by said conical annular shoulder surface with said axis, wherein said implant comprises a metal main body forming the most part of said anchoring part and the first implant end, wherein said implant flyer comprises one of an annular ceramic body which is secured to the metal main body and forms at least an outer portion of said annular shoulder surface and a ceramic covering provided on a peripheral surface portion of the metal main body and extending from an outer edge of the annular shoulder surface toward the first implant end;

a body which is adapted for supporting one of a crown of an individual artificial tooth, a part of a bridge and a part of a prosthesis with a plurality of artificial teeth, said body being attachable to the implant having a conical bearing surface and conical inner surface forming a continuous axial hole; and a screw having an external thread, wherein, when the body is attached to the implant, the screw is partially lodged within the hole of said body and is screwed with its external thread into the internal thread of the inner wall of the implant, so that the annular bearing surface of said body lies on the annular shoulder surface of the implant and that the second conical head portion supports the conical inner surface of said body with at most little play.

37. The device according to claim 36, wherein said body comprises an end forming said annular bearing surface and extending, when said body is attached to the implant, along said axis from an outermost edge of said annular bearing surface to said conical inner surface and said end portion of the body lies a distance outside the conical inner surface.

38. A device for holding a dental prosthesis, the device comprising:

an implant adapted to be at least partially anchored in a bone, said implant having an axis, a first implant end adapted for deepest insertion into the bone, a second implant end opposite said first implant end, and an annular shoulder surface disposed at said second implant end and forming an angle with said axis, said second implant end having a mouth and a hole formed therein where an inner wall of the second implant end has an internal thread where a conical hole portion is disposed between said internal thread and said mouth, and said conical hole portion widens from said internal thread toward said mouth; and a bolt and a ceramic body with a blind hole, wherein the bolt protrudes into the blind hole of the ceramic body in order to rigidly secured the bolt to the ceramic body, said bolt having an external thread which, when the device is assembled, is screwed into the internal thread of the implant and wherein the ceramic body to which the bolt is secured, has a conical portion which, when the device is assembled, sits firmly and free from play in the conical hole portion of the implant.

* * * * *

UNITED STATES PATENT AND TRADEMARK OFFICE
CERTIFICATE OF CORRECTION

PATENT NO. : 6,461,160 B1
DATED : October 8, 2002
INVENTOR(S) : Franz Sutter

It is certified that error appears in the above-identified patent and that said Letters Patent is hereby corrected as shown below:

<u>Column 23,</u>
Line 17, "said implant flyer comprises" should read as -- said implant further comprises --.

Signed and Sealed this

Eleventh Day of November, 2003

JAMES E. ROGAN
*Director of the United States Patent and Trademark Office*